(12) United States Patent
Allard et al.

(10) Patent No.: US 9,370,477 B2
(45) Date of Patent: Jun. 21, 2016

(54) DYEING COMPOSITION COMPRISING A FATTY SUBSTANCE, A PYRAZOLOPYRIDINE OXIDATION BASE AND A COUPLER

(75) Inventors: Delphine Allard, Paris (FR); Valérie Nicou, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/994,281

(22) PCT Filed: Dec. 14, 2011

(86) PCT No.: PCT/EP2011/072745
§ 371 (c)(1),
(2), (4) Date: Aug. 5, 2013

(87) PCT Pub. No.: WO2012/080324
PCT Pub. Date: Jun. 21, 2012

(65) Prior Publication Data
US 2013/0312203 A1 Nov. 28, 2013

Related U.S. Application Data
(60) Provisional application No. 61/432,723, filed on Jan. 14, 2011.

(30) Foreign Application Priority Data
Dec. 17, 2010 (FR) ..................................... 10 60762

(51) Int. Cl.
A61Q 5/10 (2006.01)
C07D 515/02 (2006.01)
A61K 8/49 (2006.01)
C07D 471/04 (2006.01)
A61K 8/36 (2006.01)

(52) U.S. Cl.
CPC ................. *A61K 8/4946* (2013.01); *A61K 8/36* (2013.01); *A61Q 5/10* (2013.01); *C07D 471/04* (2013.01)

(58) Field of Classification Search
CPC ............. A61Q 5/10; A61K 8/34; A61K 8/38; C07D 471/04
USPC ...................... 8/405, 406; 546/121
See application file for complete search history.

(56) References Cited

U.S. PATENT DOCUMENTS

| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,457,200 A | 10/1995 | Zimmermann et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 7,578,856 B2 | 8/2009 | Saunier |
| 2002/0050013 A1 | 5/2002 | Vidal et al. |
| 2003/0019051 A9 | 1/2003 | Vidal et al. |
| 2007/0136959 A1 | 6/2007 | Fadli |

(Continued)

FOREIGN PATENT DOCUMENTS

| DE | 23 59 399 | 5/1975 |
| DE | 38 43 892 | 6/1990 |

(Continued)

OTHER PUBLICATIONS

STIC Saech Report dated Sep. 9, 2013.*
(Continued)

*Primary Examiner* — Eisa Elhilo
(74) *Attorney, Agent, or Firm* — The Marbury Law Group, PLLC

(57) ABSTRACT

A subject-matter of the present invention is a composition for dyeing keratinous fibers, in particular human keratinous fibers, such as the hair, comprising: —at least 25% by weight of at least one fatty substance not comprising a carboxylic acid functional group; —at least one aminopyrazolopyridine oxidation base chosen from the bases of formula (I), the bases of formula (II) and their addition salts, their solvates and the solvates of their salts: —at least one coupler; and —at least one oxidizing agent. The composition of the invention is suitable for use in oxidation dyeing and results in a coloration with shades which are varied, intense or chromatic, powerful, attractive, not very selective and highly resistant to the various assaults which the hair may be subjected to, such as shampooing operations, sweat, permanent reshapings and light. In particular, it makes it possible to obtain an optimized color result with a good power, a good dyeing capacity and a good equal depth.

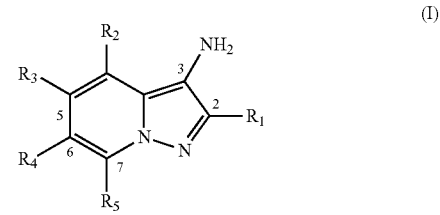

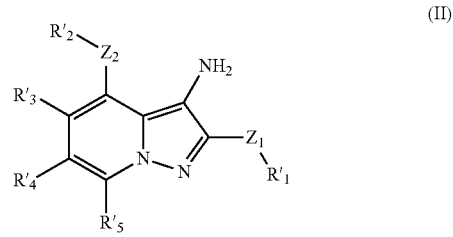

19 Claims, No Drawings

(56) References Cited

U.S. PATENT DOCUMENTS

| | | | |
|---|---|---|---|
| 2007/0143935 A1 | 6/2007 | Faldi et al. | |
| 2008/0289122 A1 | 11/2008 | Saunier | |
| 2010/0162493 A1* | 7/2010 | Audousset et al. | 8/416 |

FOREIGN PATENT DOCUMENTS

| | | |
|---|---|---|
| DE | 41 33 957 | 4/1993 |
| DE | 195 43 988 | 5/1997 |
| EP | 0 770 375 | 5/1997 |
| EP | 1 792 606 | 6/2007 |
| EP | 1 792 903 | 6/2007 |
| FR | 2 733 749 | 11/1996 |
| FR | 2 886 136 | 12/2006 |
| FR | 2 915 879 | 11/2008 |
| FR | 2 920 091 | 2/2009 |
| GB | 1 026 978 | 4/1966 |
| GB | 1 153 196 | 5/1969 |
| JP | 2-19576 | 1/1990 |
| JP | 5-163124 | 6/1993 |
| WO | 94/08969 | 4/1994 |
| WO | 94/08970 | 4/1994 |
| WO | 96/15765 | 5/1996 |
| WO | WO 2010/133640 A2 * 11/2010 | A61K 8/41 |

OTHER PUBLICATIONS

International Search Report for PCT/EP2011/072745, (2011).
Todd, Charles, et al., "Volatile Silicone Fluids for Cosmetic Formulations," Cosmetics and Toiletries, vol. 91, Jan. 1976, pp. 27-32.

* cited by examiner

DYEING COMPOSITION COMPRISING A FATTY SUBSTANCE, A PYRAZOLOPYRIDINE OXIDATION BASE AND A COUPLER

This is a national stage application of PCT/EP2011/072745, filed internationally on Dec. 14, 2011, which claims priority to U.S. Provisional Application No. 61/432,723, filed on Jan. 14, 2011; as well as French Application FR 1060762, filed on Dec. 17, 2010.

A subject-matter of the invention is a dyeing composition comprising at least 25% by weight of fatty substance, at least one specific pyrazolopyridine oxidation base, at least one coupler and at least one oxidizing agent, and the dyeing method employing this composition.

It is known to dye keratinous fibres, in particular human keratinous fibres, such as the hair, with dyeing compositions comprising oxidation dye precursors, generally known as oxidation bases, such as ortho- or para-phenylenediamines, ortho- or para-aminophenols and heterocyclic compounds. These oxidation bases are colourless or weakly coloured compounds which, in combination with oxidizing products, can give rise, by an oxidative coupling process, to coloured compounds.

It is also known that it is possible to vary the shades obtained with these oxidation bases by combining them with couplers or colouring modifiers, the latter being chosen in particular from aromatic meta-diamines, meta-aminophenols, meta-diphenols and certain heterocyclic compounds, such as indole compounds.

The variety of the molecules employed as oxidation bases and couplers makes it possible to obtain a rich palette of colours.

The "permanent" colouring obtained by virtue of these oxidation dyes furthermore has to satisfy a certain number of requirements. Thus, it must be without disadvantage toxicologically, it must make it possible to obtain shades within the desired intensity and it must behave well in the face of external agents, such as light, bad weather, washing, permanent waving, perspiration and rubbing.

The dyes must also make it possible to cover grey hair and, finally, be as non-selective as possible, that is to say make it possible to obtain the smallest possible differences in colouring along the same keratinous fibre, which is generally sensitized (i.e., damaged) to different degrees between its tip and its root.

It is already known to use oxidation bases derived from 3-aminopyrazolo[1,5-a]-pyridine in the field of the dyeing of keratinous fibres, in particular oxidation bases of formulae (I) and (II) below. In particular, such bases have been disclosed in the documents EP 1 792 903 and EP 1 792 606.

The results obtained to date are not entirely satisfactory, whether in terms of colour result or in terms of applicational qualities.

The aim of the present invention is to obtain novel compositions for dyeing keratinous fibres which do not exhibit the disadvantages of the prior art. More particularly, the aim of the present invention is to obtain novel dyeing compositions which are very effective in dyeing terms and which are easy to mix and to apply, in particular which do not flow and which remain highly localized at the point of application and which limit olfactory problems on application.

This aim is achieved with the present invention, a subject-matter of which is a composition for dyeing keratinous fibres, in particular human keratinous fibres, such as the hair, comprising:

at least 25% by weight of at least one fatty substance not comprising a carboxylic acid functional group;

at least one aminopyrazolopyridine oxidation base chosen from bases of formula (I), bases of formula (II), and their addition salts, their solvates and the solvates of their salts:

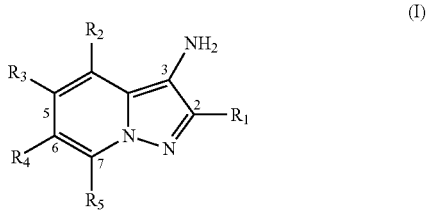

(I)

in which:
$R_1$, $R_2$, $R_3$, $R_4$ and $R_5$, which are identical or different, represent a hydrogen or halogen atom; an —$NHSO_3H$ radical; a hydroxyl radical; a ($C_1$-$C_4$)alkyl radical; a ($C_1$-$C_4$)alkoxy radical; a ($C_1$-$C_4$)alkylthio radical; a mono($C_1$-$C_4$)alkylamino radical; a di($C_1$-$C_4$)alkylamino radical in which the two alkyl groups can, in conjunction with the nitrogen atom to which they are bonded, form a ring which can be interrupted by one or more nitrogen, oxygen or sulphur atoms; a heterocycle; a nitro radical; a phenyl radical; a carbonyl radical; an alkoxy($C_1$-$C_4$)carbonyl radical; a carboxamido radical; a cyano radical; an amino radical; a sulphonyl radical; a —$CO_2H$ radical; an —$SO_3H$ radical; a —$PO_3H_2$ radical; a —$PO_4H_2$ radical; or a group:

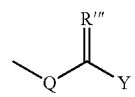

in which R''' represents an oxygen or nitrogen atom, Q represents an oxygen atom or an NH or NH($C_1$-$C_4$)alkyl group, and Y represents a hydroxyl, amino, ($C_1$-$C_4$)alkyl, ($C_1$-$C_4$)alkoxy, ($C_1$-$C_4$)alkylamino or di($C_1$-$C_4$)alkylamino radical;

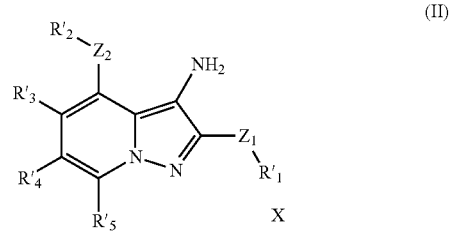

(II)

in which:
$Z_1$ and $Z_2$ independently represent:
  a single covalent bond;
  a divalent radical chosen from:
    an —$O(CH_2)_p$— radical, p denoting an integer ranging from 0 to 6;
    an —$NR'_6(CH_2)_q(C_6H_4)_t$— radical, q denoting an integer ranging from 0 to 6 and t denoting 0 or 1, $R'_6$ representing a hydrogen atom or a $C_1$-$C_6$ alkyl radical optionally substituted by one or more hydroxyl groups;
$Z_1$ can also represent a divalent radical —S—, —SO— or —$SO_2$— when $R'_1$, is a methyl radical;

$R'_1$ and $R'_2$ independently represent:
- a hydrogen;
- a $C_1$-$C_{10}$ alkyl radical, which is optionally substituted and optionally interrupted by a heteroatom or a group chosen from O, N, Si, S, SO or $SO_2$;
- a halogen;
- an $SO_3H$ radical;
- a substituted or unsubstituted and saturated, unsaturated or aromatic 5- to 8-membered ring optionally including one or more heteroatoms or groups chosen from N, O, S, $SO_2$ or —CO—, it being possible for the ring to be cationic and/or substituted by a cationic radical;
- an —$N^+R_{17}R_{18}R_{19}$ group, $R_{17}$, $R_{18}$ and $R_{19}$ being linear or branched $C_1$-$C_5$ alkyls optionally substituted by one or more hydroxyl groups;

when $Z_1$ or $Z_2$ respectively represents a covalent bond, then $R'_1$, or $R'_2$ respectively can also represent:
- an optionally substituted $C_1$-$C_6$ alkylcarbonyl radical;
- an —O—CO—R, —CO—O—R, NR—CO—R' or —CO—NRR' radical in which R and R' independently represent a hydrogen atom or an optionally substituted $C_1$-$C_6$ alkyl radical;

$R'_3$, $R'_4$ and $R'_5$, which are identical or different, represent:
- a hydrogen atom;
- a hydroxyl radical;
- a $C_1$-$C_6$ alkoxy radical;
- a $C_1$-$C_6$ alkylthio radical;
- an amino radical;
- a monoalkylamino radical;
- a di($C_1$-$C_6$)alkylamino radical in which the alkyl radicals can form, with the nitrogen atom to which they are attached, a saturated or unsaturated and aromatic or non-aromatic 5- to 8-membered heterocycle which can include one or more heteroatoms or groups chosen from N, O, S, $SO_2$ or CO, it being possible for the heterocycle to be cationic and/or substituted by a cationic radical;
- an optionally substituted $C_1$-$C_6$ alkylcarbonyl radical;
- an —O—CO—R, —CO—O—R, NR—CO—R' or —CO—NRR' radical with R and R' as defined above;
- a halogen;
- an —$NHSO_3H$ radical;
- an optionally substituted $C_1$-$C_4$ alkyl radical;
- a saturated, unsaturated or aromatic carbon ring which is optionally substituted;
- $R'_3$, $R'_4$ and $R'_5$ can form, in pairs, a ring which is or is not partially saturated;

X represents an ion or a group of ions which makes it possible to provide the electrical neutrality of the derivative of formula (II);

with the condition that at least one of the groups $R'_1$, and $R'_2$ represents a cationic radical;
- at least one coupler; and
- at least one oxidizing agent.

The invention also relates to a method for treating human keratinous fibres starting from this composition.

A subject-matter of the invention is likewise a two-compartment device comprising, in one, a first composition including at least one fatty substance not comprising a carboxylic acid functional group, at least one specific pyrazolopyridine oxidation base and at least one coupler and, in the other, a second composition including at least one oxidizing agent.

Finally, the invention relates to a three-compartment device comprising, in one, a composition including at least one fatty substance not comprising a carboxylic acid functional group, in another, a composition including at least one specific pyrazolopyridine oxidation base and at least one coupler and, in the last, a composition including at least one oxidizing agent.

The compositions of the various devices are intended to be mixed to give the composition according to the invention, immediately before application to the keratinous fibres.

The composition of the present invention makes it possible in particular to obtain a composition for dyeing keratinous fibres which is suitable for use in oxidation dyeing and results in a coloration with shades which are varied, intense or chromatic, powerful, attractive, not very selective and highly resistant to the various assaults which the hair may be subjected to, such as shampooing operations, sweat, permanent reshapings and light. In particular, the composition in accordance with the invention makes it possible to obtain an optimized colour result with a good power, a good dyeing capacity and a good equal depth.

Other characteristics and advantages of the invention will become more clearly apparent on reading the description and examples which follow.

In the context of the present invention, the expression "at least one" is equivalent to the expression "one or more".

The present invention also covers the mesomeric forms and the stereoisomers of the various oxidation dyes of the invention.

It should be noted that, in the text hereinbelow, unless otherwise indicated, the limits of a range of values are included in that range.

As indicated above, the composition according to the invention comprises at least 25% by weight of at least one fatty substance not comprising a carboxylic acid functional group.

The term "fatty substance" means an organic compound that is insoluble in water at ordinary temperature (25° C.) and at atmospheric pressure (760 mmHg; i.e. $1.013 \times 10^5$ Pa) (solubility of less than 5% and preferably of less than 1%, more preferably still of less than 0.1%). They have in their structure at least one hydrocarbon chain comprising at least 6 carbon atoms or a sequence of at least two siloxane groups. In addition, the fatty substances are soluble in organic solvents under the same temperature and pressure conditions, for instance chloroform, ethanol or benzene.

In the context of the invention, the term "fatty substance not comprising a carboxylic acid functional group" denotes a fatty substance not comprising a —COOH group or a —COO— group.

According to the invention, the fatty substances are preferably chosen from compounds which are liquid or pasty at ambient temperature and at atmospheric pressure.

More particularly, the fatty substances are chosen from lower $C_6$-$C_{16}$ alkanes, non-silicone oils of animal, vegetable or synthetic origin, hydrocarbons of mineral or synthetic origin, fatty alcohols, fatty acid and/or fatty alcohol esters, non-silicone waxes or silicones.

It is recalled that, for the purposes of the invention, fatty alcohols and esters more particularly have at least one saturated or unsaturated and linear or branched hydrocarbon group containing 6 to 30 carbon atoms, which is optionally substituted, in particular with one or more (in particular 1 to 4) hydroxyl groups. If they are unsaturated, these compounds can comprise from one to three conjugated or nonconjugated carbon-carbon double bonds.

As regards the lower alkanes, the latter comprise from 6 to 16 carbon atoms and are linear or branched, optionally cyclic. Mention may be made, by way of example, of hexane, undecane, dodecane, tridecane or isoparaffins, such as isohexadecane and isodecane.

Mention may be made, as oils of animal, vegetable or synthetic origin which can be used in the composition of the invention, for example, of:

hydrocarbon oils of animal origin, such as perhydrosqualene;

triglyceride oils of vegetable or synthetic origin, such as liquid triglycerides of fatty acids comprising from 6 to 30 carbon atoms, such as triglycerides of heptanoic or octanoic acids or also, for example, sunflower oil, maize oil, soybean oil, cucumber oil, grape seed oil, sesame oil, hazelnut oil, apricot oil, macadamia oil, arara oil, castor oil, avocado oil, triglycerides of caprylic/capric acids, such as those sold by Stearineries Dubois or those sold under the names Miglyol® 810, 812 and 818 by Dynamit Nobel, jojoba oil or shea butter oil.

linear or branched hydrocarbons of mineral or synthetic origin of more than 16 carbon atoms, such as volatile or non-volatile liquid paraffins and their derivatives, petrolatum, liquid petrolatum, polydecenes or hydrogenated polyisobutene, such as Parleam®.

fluorinated oils, such as perfluoromethylcyclopentane and perfluoro-1,3-dimethyl-cyclohexane, sold under the names of "Flutec® PC1" and "Flutec® PC3" by BNFL Fluorochemicals; perfluoro-1,2-dimethylcyclobutane; perfluoroalkanes, such as dodecafluoropentane and tetradecafluorohexane, sold under the names "PF 5050®" and "PF 5060®" by 3M, or bromoperfluorooctyl, sold under the name "Foralkyl®" by Atochem; nonafluoromethoxybutane and nonafluoroethoxyisobutane; or perfluoromorpholine derivatives, such as 4-(trifluoromethyl)perfluoromorpholine, sold under the name "PF 5052®" by 3M.

The fatty alcohols that are suitable for the use of the invention are more particularly chosen from saturated or unsaturated and linear or branched alcohols containing from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

As regards the fatty acid and/or fatty alcohol esters, which are advantageously different from the abovementioned triglycerides, mention may in particular be made of esters of saturated or unsaturated and linear or branched $C_1$-$C_{26}$ aliphatic mono- or polyacids and of saturated or unsaturated and linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition can also comprise, as fatty ester, esters and diesters of sugars and of $C_6$-$C_{30}$, preferably $C_{12}$-$C_{22}$, fatty acids. It should be remembered that "sugar" is understood to mean oxygen-comprising hydrocarbon compounds which have several alcohol functional groups, with or without an aldehyde or ketone functional group, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The esters of sugars and of fatty acids can be chosen in particular from the group consisting of the esters or mixtures of esters of sugars described above and of saturated or unsaturated and linear or branched $C_6$-$C_{30}$, preferably $C_{12}$-$C_{22}$, fatty acids. If they are unsaturated, these compounds can comprise from one to three conjugated or nonconjugated carbon-carbon double bonds.

The esters according to this alternative form can also be chosen from mono-, di-, tri- and tetraesters, polyesters and their mixtures.

These esters may be, for example, oleates, laurates, palmitates, myristates, behenates, cocoates, stearates, linoleates, linolenates, caprates or arachidonates, or mixtures thereof such as, especially, oleate/palmitate, oleate/stearate and palmitate/stearate mixed esters.

More particularly, use is made of mono- and diesters and in particular of sucrose, glucose or methylglucose mono- or dioleates, -stearates, -behenates, -oleate/palmitates, -linoleates, -linolenates or -oleate/stearates.

Mention may be made, by way of example, of the product sold under the name Glucate® DO by Amerchol, which is a methylglucose dioleate.

Examples of esters or mixtures of esters of sugar and of fatty acid that may also be mentioned include:

the products sold under the names F160, F140, F110, F90, F70 and SL40 by Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester, triester and polyester;

sucrose monopalmitate/stearate and dipalmitate/stearate, sold by Goldschmidt under the name Tegosoft® PSE.

The (non-silicone) wax(es) are chosen especially from carnauba wax, candelilla wax, esparto grass wax, paraffin wax, ozokerite, vegetable waxes, for instance olive wax, rice wax, hydrogenated jojoba wax or the absolute waxes of flowers such as the essential wax of blackcurrant blossom sold by Bertin (France), animal waxes, for instance beeswaxes, or modified beeswaxes (cerabellina); other waxes or waxy starting materials that may be used according to the invention are especially marine waxes such as the product sold by Sophim under the reference M82, and polyethylene waxes or polyolefin waxes in general.

The silicones that may be used in the cosmetic compositions of the present invention are volatile or non-volatile and cyclic, linear or branched silicones, which are unmodified or modified with organic groups, having a viscosity from $5 \times 10^{-6}$ to 2.5 m$^2$/s at 25° C., and preferably from $1 \times 10^{-5}$ to 1 m$^2$/s.

The silicones that may be used in accordance with the invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxyalkylene) groups, amine groups and alkoxy groups.

Organopolysiloxanes are defined in greater detail in Walter Noll's "Chemistry and Technology of Silicones" (1968), Academic Press. They may be volatile or non-volatile.

When they are volatile, the silicones are chosen more particularly from those having a boiling point of between 60° C. and 260° C. and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by Union Carbide, of formula:

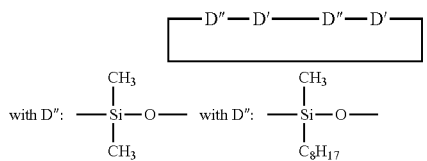

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis[2,2,2',2',3,3'-hexa(trimethylsilyloxy)-neopentane];

(ii) volatile linear polydialkylsiloxanes having from 2 to 9 silicon atoms and exhibiting a viscosity of less than or equal to $5 \times 10^{-6}$ m$^2$/s at 25° C. These are, for example, decamethyltetrasiloxane, sold in particular under the name "SH 200" by Toray Silicone. Silicones coming within this category are also described in the paper published in Cosmetics and Toiletries, Vol. 91, January 76, pp. 27-32—TODD & BYERS "Volatile Silicone Fluids for Cosmetics".

Use is preferably made of nonvolatile polydialkylsiloxanes, polydialkylsiloxane gums and resins, polyorganosiloxanes modified by the above organofunctional groups and their mixtures.

These silicones are more particularly chosen from polydialkylsiloxanes, among which mention may be made mainly of polydimethylsiloxanes containing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by Rhodia;

the oils of the 200 series from Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from Rhodia.

Mention may also be made, in this category of polydialkylsiloxanes, of the products sold under the names "Abil Wax® 9800 and 9801" by Goldschmidt, which are polydi($C_1$-$C_{20}$) alkylsiloxanes.

The silicone gums that can be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:

mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;

mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in SF 1202 Silicone Fluid oil corresponding to decamethylcyclo-pentasiloxane;

mixtures of two PDMSs with different viscosities, and more particularly of a PDMS gum and a PDMS oil, such as the product SF 1236 from General Electric. The product SF 1236 is the mixture of an SE 30 gum defined above, having a viscosity of 20 m$^2$/s, and of an SF 96 oil, with a viscosity of $5 \times 10^{-6}$ m$^2$/s. This product preferably comprises 15% of SE 30 gum and 85% of SF 96 oil.

The organopolysiloxane resins that can be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents an alkyl containing 1 to 16 carbon atoms. Those which are particularly preferred among these products are those in which R denotes a lower $C_1$-$C_4$ alkyl group, more particularly methyl.

Among these resins, mention may be made of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type sold in particular under the names X22-4914, X21-5034 and X21-5037 by Shin-Etsu.

The organomodified silicones that can be used in accordance with the invention are silicones as defined above and comprising in their structure one or more organofunctional groups attached via a hydrocarbon group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are chosen in particular from polydimethyl/methyl-phenylsiloxanes or polydimethyl/diphenylsiloxanes which are linear and/or branched and which have a viscosity ranging from $1 \times 10^{-5}$ to $5 \times 10^{-2}$ m$^2$/s at 25° C.

Mention may be made, among these polyalkylarylsiloxanes, by way of example, of the products sold under the following names:

the Silbione® oils of the 70 641 series from Rhodia;

the oils of the series Rhodorsil® 70 633 and 763 from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH 1000;

certain oils of the SF series from General Electric, such as SF 1023, SF 1154, SF 1250 and SF 1265.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol, sold by Dow Corning under the name DC 1248, or the oils Silwet® L 722, L 7500, L 77 and L 711 from Union Carbide, and the ($C_{12}$)alkyl methicone copolyol, sold by Dow Corning under the name Q2 5200;

substituted or unsubstituted amine groups, such as the products sold under the name GP 4 Silicone Fluid and GP 7100 by Genesee, or the products sold under the names Q2 8220 and Dow Corning 929 or 939 by Dow Corning. The substituted amine groups are in particular $C_1$-$C_4$ aminoalkyl groups;

alkoxyl groups, such as the product sold under the name "Silicone Copolymer F-755" by SWS Silicones and the products sold under the names Abil Wax® 2428, 2434 and 2440 by Goldschmidt.

More particularly, the fatty substances are chosen from the compounds which are liquid or pasty at ambient temperature and at atmospheric pressure, preferably liquid.

The fatty substances are preferably chosen from lower $C_6$-$C_{16}$ alkanes, fatty alcohols, fatty acid esters, fatty alcohol esters, oils, in particular mineral, vegetable or synthetic non-silicone oils, or silicones.

Preferably, the fatty substance is chosen from liquid petrolatum, polydecenes, liquid fatty acid and/or fatty alcohol esters, liquid fatty alcohols and their mixtures.

The composition according to the invention comprises at least 25% by weight of fatty substance. More particularly, it comprises a content of fatty substance ranging from 25 to 80% by weight, more preferably still from 25 to 65% by weight and better still from 30 to 55% by weight, with respect to the total weight of the composition.

In the context of the invention and unless otherwise indicated, the expression "alkyl" used for the alkyl radicals and for the groups comprising an alkyl part means a linear or branched carbon chain comprising from 1 to 4 carbon atoms which is unsubstituted or substituted by one or more heterocycles or by one or more phenyl groups or by one or more groups chosen from halogen atoms, such as chlorine, bromine, iodine and fluorine; hydroxyl, alkoxyl, amino, carbonyl, carboxamido, sulphonyl, —CO$_2$H, —SO$_3$H, —PO$_3$H$_2$, —PO$_4$H$_2$, —NHSO$_3$H, sulphonamido, mono($C_1$-$C_4$)alkylamino or tri($C_1$-$C_4$)alkylammonium radicals, or a di($C_1$-$C_4$) alkylamino radical in which the two alkyl groups can form, together with the nitrogen atom of the said di($C_1$-$C_4$)alkylamino group to which they are bonded, a ring which can be interrupted by one or more nitrogen, oxygen or sulphur atoms.

Likewise, according to the invention, the expression "alkoxy" used for the alkoxy radicals and for the groups comprising an alkoxy part, means a linear or branched O-carbon chain comprising from 1 to 4 carbons which is unsubstituted or substituted by one or more groups chosen from heterocycles; halogen atoms, such as chlorine, bromine, iodine and fluorine; hydroxyl, amino, carbonyl, carboxamido, sulphonyl, —CO$_2$H, —SO$_3$H, —PO$_3$H$_2$, —PO$_4$H$_2$, —NHSO$_3$H, sulphonamido, mono($C_1$-$C_4$)alkylamino or tri ($C_1$-$C_4$)alkylammonium radicals or a di($C_1$-$C_4$)alkylamino radical in which the two alkyl groups can form, together with the nitrogen atom of the said di($C_1$-$C_4$)alkylamino group to which they are bonded, a ring which can be interrupted by one or more nitrogen, oxygen or sulphur atoms.

According to the invention, the term "heterocycle" is understood to mean a 5-, 6-, 7- or 8-membered aromatic or nonaromatic ring comprising from 1 to 3 heteroatoms chosen from nitrogen, sulphur and oxygen atoms. These heterocycles can be fused to other heterocycles or to a phenyl group. They can be substituted by a halogen atom; a ($C_1$-$C_4$)alkyl radical; a ($C_1$-$C_4$)alkoxy radical; a hydroxyl radical; an amino radical; a ($C_1$-$C_4$)alkylamino radical; or a di($C_1$-$C_4$)alkylamino radical in which the two alkyl groups can form, together with the nitrogen atom to which they are bonded, a ring which can be interrupted by one or more nitrogen, oxygen or sulphur atoms. In addition, these heterocycles can be quaternized by a ($C_1$-$C_4$)alkyl radical.

Mention may in particular be made, among these optionally fused heterocycles, by way of example, of the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl)benzothiazol-3-ium and 1-(2-hydroxyethyl)-pyridinium.

According to the invention, the term "phenyl" is understood to mean a phenyl radical which is unsubstituted or substituted by one or more cyano, carbonyl, carboxamido, sulphonyl, —CO$_2$H, —SO$_3$H, —PO$_3$H$_2$, —PO$_4$H$_2$, hydroxyl, amino, mono($C_1$-$C_4$)alkylamino or di($C_1$-$C_4$)alkylamino radicals, in which, in the di($C_1$-$C_4$)alkyl-amino radical, the two alkyl groups can form, together with the nitrogen atom of the said di($C_1$-$C_4$)alkylamino group to which they are bonded, a ring which can be interrupted by one or more nitrogen, oxygen or sulphur atoms.

Mention may in particular be made, among the

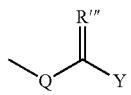

groups, of the acetamide, dimethylurea, O-methylcarbamate, methyl carbonate, N,N-dimethyl-carbamate and ester groups.

Preference is given, among the compounds of formula (I) above, to the 3-aminopyrazolo[1,5-a]pyridines corresponding to the following formula (I'), and to their addition salts, their solvates and the solvates of their salts:

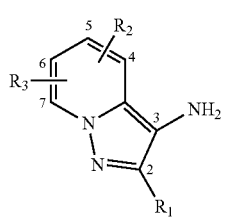

in which:
$R_1$, $R_2$, $R_3$, which are identical or different, represent a hydrogen or halogen atom; a hydroxyl radical; a ($C_1$-$C_4$)alkyl radical; a ($C_1$-$C_4$)alkylthio radical; a ($C_1$-$C_4$)alkoxy radical; an —$NHSO_3H$ radical; an amino radical; a ($C_1$-$C_4$)alkylamino radical; a di($C_1$-$C_4$)alkylamino radical in which the two alkyl groups can form, together with the nitrogen atom to which they are bonded, a ring which can be interrupted by one or more nitrogen, oxygen or sulphur atoms; a heterocycle as defined above; a sulphonamido radical; a carbonyl radical; a ($C_1$-$C_4$)alkoxycarbonyl radical; a carboxamido radical; or a group of formula:

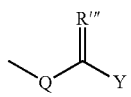

in which R'''represents an oxygen or nitrogen atom, Q represents an oxygen atom or an NH or NH($C_1$-$C_4$)alkyl group, and Y represents a hydroxyl, amino, $C_1$-$C_4$ alkyl, ($C_1$-$C_4$) alkoxy, ($C_1$-$C_4$)alkylamino or di($C_1$-$C_4$)alkylamino radical.

Mention may in particular be made, among the 3-aminopyrazolo[1,5-a]pyridines of formula (I) which can be used as oxidation base in the dyeing compositions in accordance with the invention, of:
pyrazolo[1,5-a]pyridin-3-ylamine;
2-(acetylamino)pyrazolo[1,5-a]pyridin-3-ylamine;
2-(morpholin-4-yl)pyrazolo[1,5-a]pyridin-3-ylamine;
3-aminopyrazolo[1,5-a]pyridine-2-carboxylic acid;
2-methoxypyrazolo[1,5-a]pyridin-3-ylamine;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-(morpholin-4-yl)pyrazolo[1,5-a]pyridin-3-ylamine;
pyrazolo[1,5-a]pyridine-3,5-diamine;
5-(morpholin-4-yl)pyrazolo[1,5-a]pyridin-3-ylamine;
2-[(3-aminopyrazolo[1,5-a]pyridin-5-yl)(2-hydroxyethyl) amino]ethanol;
2-[(3-aminopyrazolo[1,5-a]pyridin-7-yl)(2-hydroxyethyl) amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-amino-pyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-(pyridin-3-yl)ethyl)pyrazolo[1,5-a]pyridine-2,3-diamine;
and their addition salts, their solvates and the solvates of their salts.

2-[(3-Aminopyrazolo[1,5-a]pyridin-2-yl)oxy]ethanol and its addition salts, its solvates and the solvates of its salts are particularly preferred among the bases described above.

The great majority of the 3-aminopyrazolo[1,5-a]pyridines of formula (I) are compounds known in the pharmaceutical field and are described in particular in U.S. Pat. No. 5,457, 200. These compounds can be prepared according to methods of synthesis well known in the literature and as described, for example, in U.S. Pat. No. 5,457,200.

The term "cationic ring or heterocycle" is understood to mean a ring comprising one or more quaternary ammonium groups.

Mention may be made, as example of radicals of the —$N^+R_{17}R_{18}R_{19}$ type, of the trimethylammonium, triethylammonium, dimethylethylammonium, diethylmethyl-ammonium, diisopropylmethylammonium, diethylpropylammonium, (β-hydroxyethyl)-diethylammonium, di(β-hydroxyethyl)methylammonium or tri(β-hydroxyethyl)-ammonium radicals.

Mention may be made, as example of cationic heterocycle, of the imidazolium, pyridinium, piperazinium, pyrrolidinium, morpholinium, pyrimidinium, thiazolium, benzimidazolium, benzothiazolium, oxazolium, benzotriazolium, pyrazolium, triazolium or benzoxazolium heterocycles.

Mention may be made, as example of cationic heterocycle, of the imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums or benzoxazoliums.

The compounds of formula (II) can optionally be salified with strong inorganic acids, such as, for example, HCl, HBr, HI, $H_2SO_4$ or $H_3PO_4$, or organic acids, such as, for example, acetic acid, lactic acid, tartaric acid, citric acid or succinic acid, benzenesulphonic acid, para-toluenesulphonic acid, formic acid or methanesulphonic acid.

If they possess anionic groups, such as the —$CO_2H$, —$SO_3H$, —$PO_3H_2$ or —$PO_4H_2$ groups, the compounds of formula (I) can be salified with alkali metal or alkaline earth metal hydroxides, such as sodium hydroxide or potassium hydroxide, with aqueous ammonia or with organic amines.

The compounds of formula (I) or (II) can also be in the form of solvates, for example a hydrate or a solvate of a linear or branched alcohol, such as ethanol or isopropanol.

Mention may be made, as examples of derivatives of formula (II), of the following compounds, in which $X^-$ is as defined above:

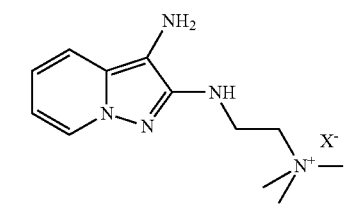

[2-(3-Aminopyrazolo[1,5-a]pyridin-2-ylamino)ethyl]trimethylammonium salt

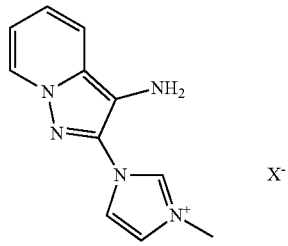

3-(3-Aminopyrazolo[1,5-a]pyridin-2-yl)-methyl-3H-imidazol-1-ium salt

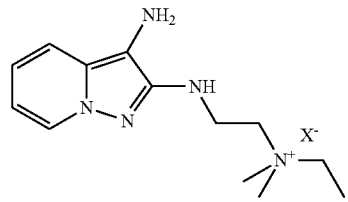

[2-(3-Aminopyrazolo[1,5-a]pyridin-2-ylamino)ethyl]ethyldimethylammonium salt

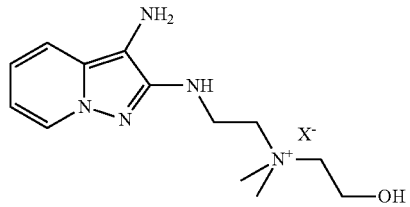

[2-(3-Aminopyrazolo[1,5-a]pyridin-2-ylamino)ethyl](2-hydroxyethyl)dimethylammonium salt

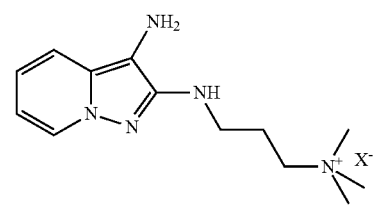

[3-(3-Aminopyrazolo[1,5-a]pyridin-2-ylamino)propyl]trimethylammonium salt

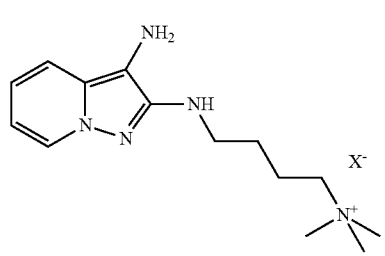

[4-(3-Aminopyrazolo[1,5-a]pyridin-2-ylamino)butyl]trimethylammonium salt

-continued

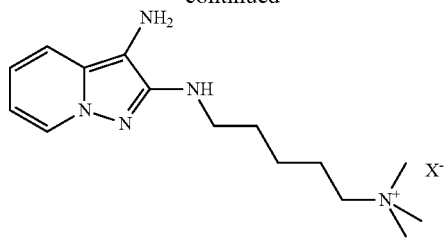

[5-(3-Aminopyrazolo[1,5-a]pyridin-2-ylamino)pentyl]trimethylammonium salt

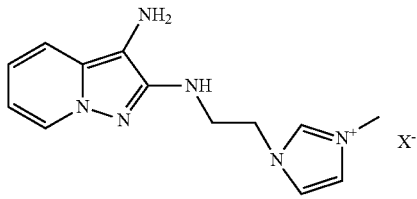

3-[2-(3-Aminopyrazolo[1,5-a]pyridin-2-ylamino)ethyl]-1-methyl-3H-imidazol-1-ium salt

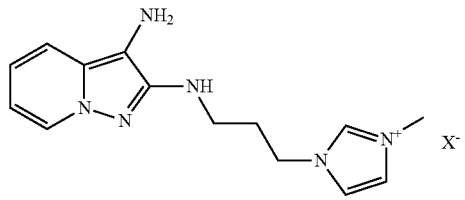

3-[3-(3-Aminopyrazolo[1,5-a]pyridin-2-ylamino)propyl]-1-methyl-3H-imidazol-1-ium salt

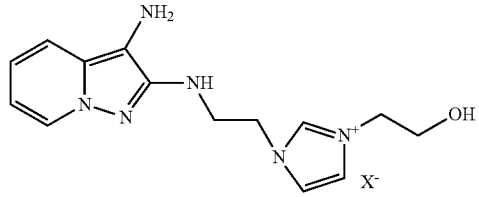

3-[3-(3-Aminopyrazolo[1,5-a]pyridin-2-ylamino)propyl]-1-(2-hydroxyethyl)-3H-imidazol-1-ium salt

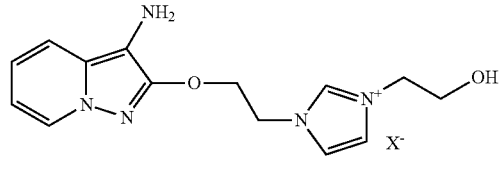

3-[2-(3-Aminopyrazolo[1,5-a]pyridin-2-yloxy)ethyl]-1-(2-hydroxyethyl)-3H-imidazol-1-ium salt

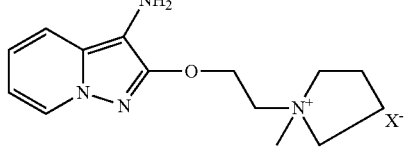

1-{2-[(3-Aminopyrazolo[1,5-a]pyridin-2-yl)oxy]ethyl}-1-methylpyrrolidinium salt

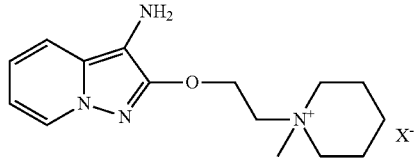

1-{2-[(3-Aminopyrazolo[1,5-a]pyridin-2-yl)oxy]ethyl}-1-methylpiperdinium salt

-continued

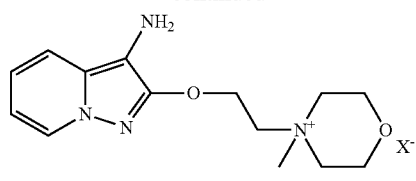

4-{2-[(3-Aminopyrazolo[1,5-a]pyridin-2-yl)oxy]ethyl}-4-methylmorpholin-4-ium salt

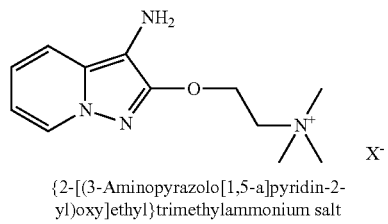

{2-[(3-Aminopyrazolo[1,5-a]pyridin-2-yl)oxy]ethyl}trimethylammonium salt

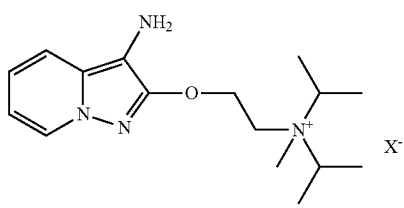

{2-[(3-Aminopyrazolo[1,5-a]pyridin-2-yl)oxy]ethyl}diisopropylmethylammonium salt

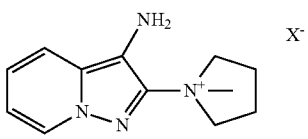

1-(3-Aminopyrazolo[1,5-a]pyridin-2-yl)-1-methylpyrrolidinium salt

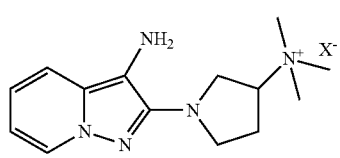

[1-(3-Aminopyrazolo[1,5-a]pyridin-2-yl)pyrrolidin-3-yl]trimethylammonium salt

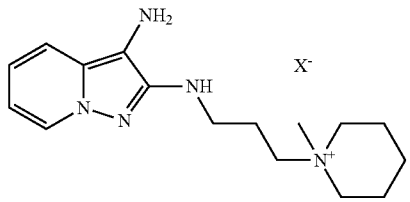

1-[3-(3-Aminopyrazolo[1,5-a]pyridin-2-ylamino)propyl]-1-methylpiperidinium salt

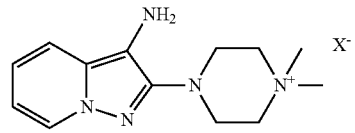

4-(3-Aminopyrazolo[1,5-a]pyridin-2-yl)-1,1-dimethylpiperazin-1-ium salt

-continued

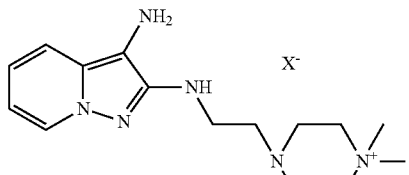

4-[2-(3-Aminopyrazolo[1,5-a]pyridin-2-ylamino)ethyl]-1,1-dimethylpiperazin-1-ium salt

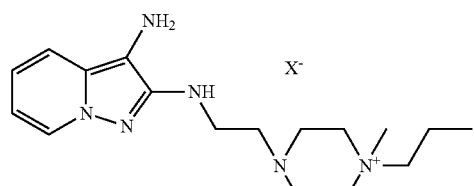

4-[2-(3-Aminopyrazolo[1,5-a]pyridin-2-ylamino)ethyl]-1-methyl-1-propylpiperazin-1-ium salt

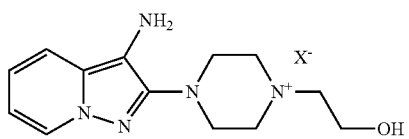

4-(3-Aminopyrazolo[1,5-a]pyridin-2-yl)-1-(2-hydroxyethyl)piperazin-1-ium salt

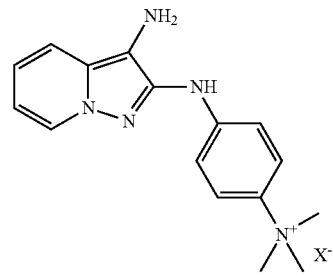

[4-(3-Aminopyrazolo[1,5-a]pyridin-2-ylamino)phenyl]trimethylammonium salt

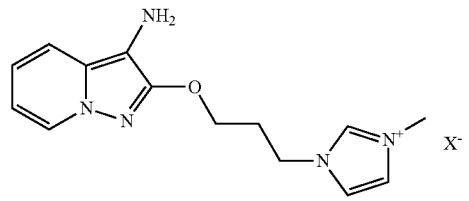

3-[3-(3-Aminopyrazolo[1,5-a]pyridin-2-yloxy)propyl]-1-methyl-3H-imidazol-1-ium salt

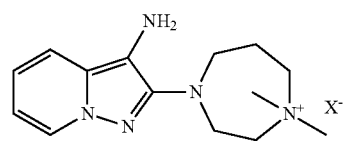

4-(3-Aminopyrazolo[1,5-a]pyridin-2-yl)-1,1-dimethyl-[1,4]-diazepan-1-ium salt

-continued

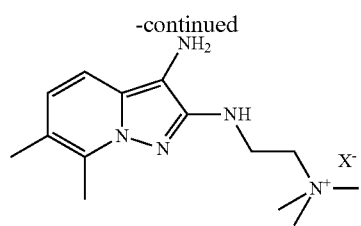

[2-(3-Amino-6,7-dimethylpyrazolo[1,5-a]pyridine-2-ylamino)ethyl]trimethylammonium salt

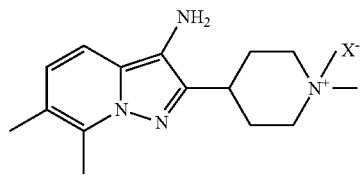

4-(3-Amino-6,7-dimethylpyrazolo[1,5-a]pyridin-2-yl)-1,1-dimethylpiperazin-1-ium-salt

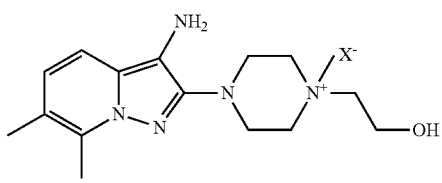

4-(3-Amino-6,7-dimethylpyrazolo[1,5-a]-pyridin-2-yl)-1-(2-hydroxyethyl)-1-methylpiperazin-1-ium-salt

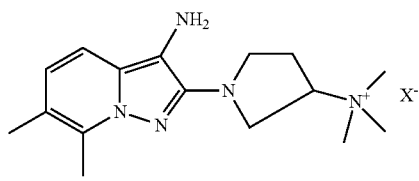

[1-(3-Amino-6,7-dimethylpyrazolo[1,5-a]-pyridin-2-yl)pyrrolidin-3-yl]trimethylammonium salt

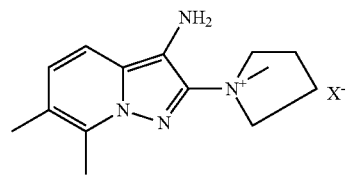

[1-(3-Amino-6,7-dimethylpyrazolo[1,5-a]pyridin-2-yl)-1-1-methylpyrrolidinium salt

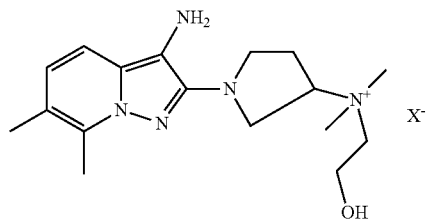

[1-(3-Amino-6,7-dimethylpyrazolo[1,5-a]-pyridin-2-yl)pyrrolidin-3-yl]-(2-hydroxyethyl)dimethylammonium salt -continued

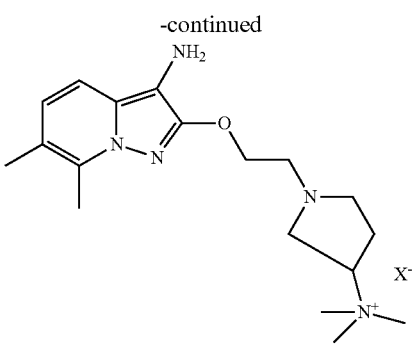

{1-[2-(3-Amino-6,7-dimethylpyrazolo[1,5-a]-pyridin-2-yloxy)ethyl]pyrrolidin-3-yl}trimethylammonium salt

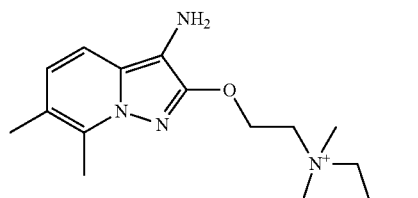

1-{2-[(3-Amino-6,7-dimethylpyrazolo[1,5-a]pyridin-2-yl)oxy]ethyl}-1-methylpyrrolidinium salt

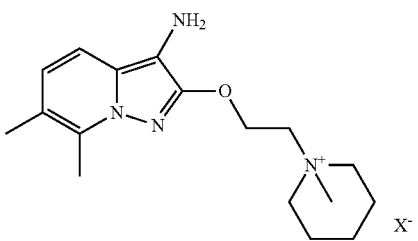

1-{2-[(3-Amino-6,7-dimethylpyrazolo[1,5-a]pyridin-2-yl)oxy]ethyl}-1-methylpiperidinium salt

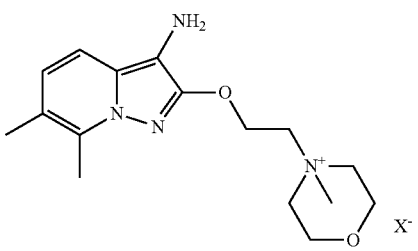

4-{2-[(3-Amino-6,7-dimethylpyrazolo[1,5-a]pyridin-2-yl)oxy]ethyl}-4-methylmorpholin-4-ium salt

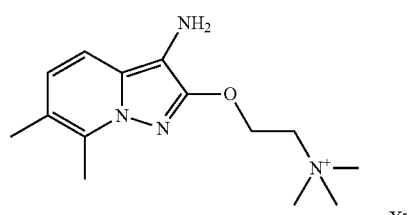

{2-[(3-Amino-6,7-dimethylpyrazolo[1,5-a]pyridin-2-yl)oxy]ethyl}trimethylammonium salt -continued

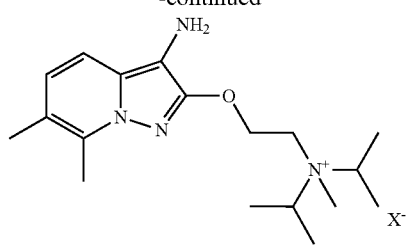

{2-[(3-Amino-6,7-dimethylpyrazolo[1,5-a]pyridin-2-yl)oxy]ethyl}diisopropylmethylammonium salt

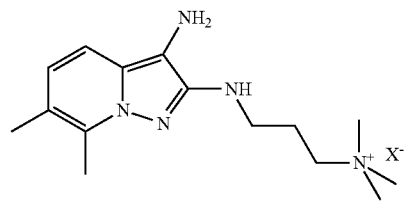

[3-(3-Amino-6,7-dimethylpyrazolo[1,5-a]pyridin-2-ylamino)propyl]trimethylammonium salt

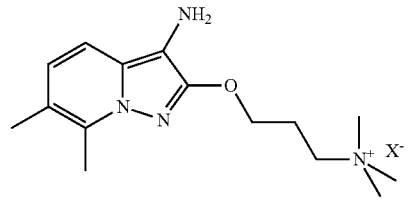

[3-(3-Amino-6,7-dimethylpyrazolo[1,5-a]pyridin-2-yloxy)propyl]trimethylammonium salt

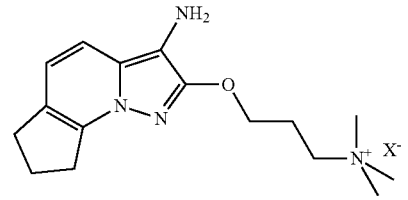

[3-(3-Amino-7,8-dihydro-6H-cyclopenta[e]pyrazolo[1,5-a]pyridin-2-yloxy)propyl]trimethyl-ammonium salt

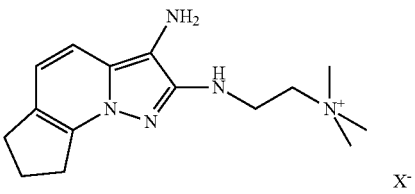

{2-[(3-Amino-7,8-dihydro-6H-cyclopenta[e]pyrazolo[1,5-a]pyridin-2-yl)amino]ethyl}trimethyl-ammonium salt

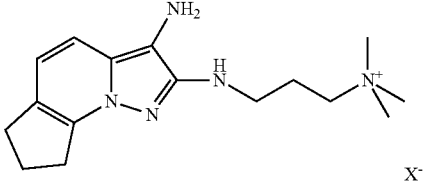

{3-[(3-Amino-7,8-dihydro-6H-cyclopenta[e]pyrazolo[1,5-a]pyridin-2-yl)amino]propyl}trimethyl-ammonium salt -continued

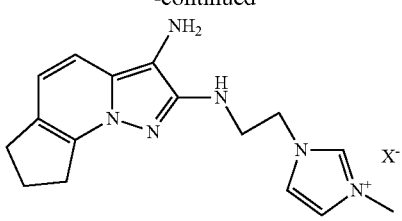

1-{2-[(3-Amino-7,8-dihydro-6H-cyclopenta[e]pyrazolo[1,5-a]pyridin-2-yl)amino]ethyl}-3-methyl-1H-imidazol-3-ium salt

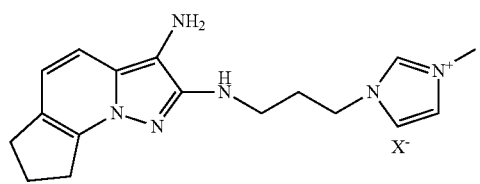

1-{3-[(3-Amino-7,8-dihydro-6H-cyclopenta[e]pyrazolo[1,5-a]pyridin-2-yl)amino]propyl}-3-methyl-1H-imidazol-3-ium salt

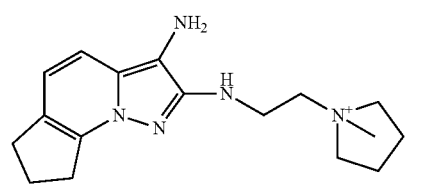

1-{2-[(3-Amino-7,8-dihydro-6H-cyclopenta[e]pyrazolo[1,5-a]pyridin-2-yl)amino]ethyl}-1-methylpyrrolidinium salt

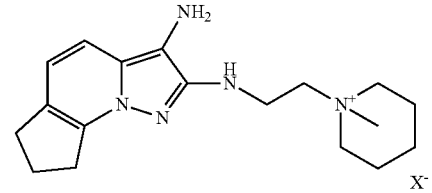

1-{2-[(3-Amino-7,8-dihydro-6H-cyclopenta[e]pyrazolo[1,5-a]pyridin-2-yl)amino]ethyl}-1-methylpiperidinium salt

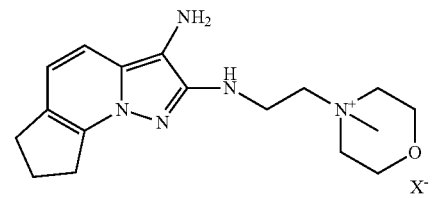

4-{2-[(3-Amino-7,8-dihydro-6H-cyclopenta[e]pyrazolo[1,5-a]pyridin-2-yl)amino]ethyl}-4-methylmorpholin-4-ium salt

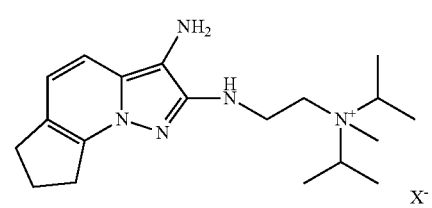

{2-[(3-Amino-7,8-dihydro-6H-cyclopenta[e]pyrazolo[1,5-a]pyridin-2-yl)amino]ethyl}diisopropyl-methylammonium salt -continued

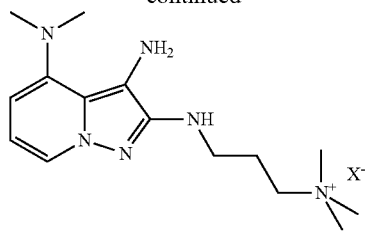

[3-(3-Amino-4-dimethylaminopyrazolo[1,5-a]-
pyridin-2-ylamino)propyl]trimethylammonium
salt

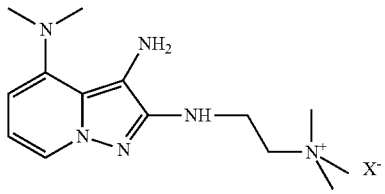

[2-(3-Amino-4-(dimethylamino)pyrazolo[1,5-a]-
pyridin-2-ylamino)ethyl]trimethylammonium
salt

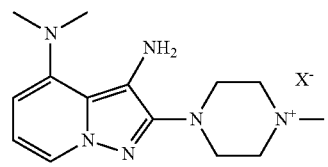

4-(3-Amino-4-(dimethylamino)pyra-
zolo[1,5-a]-pyridin-2-yl)-1-
methylpiperazin-1-ium-salt

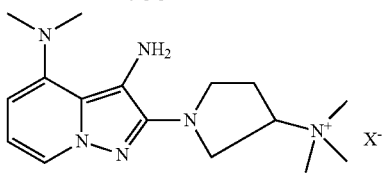

[1-(3-Amino-4-(dimethylamino)pyrazolo[1,5-
a]-pyridin-2-yl)pyrrolidin-3-
yl]trimethylammonium salt

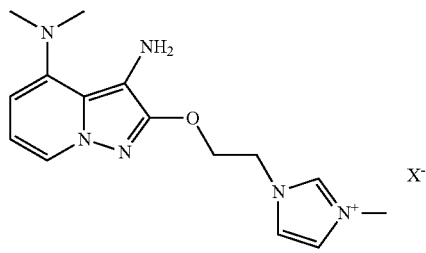

3-[2-(3-Amino-4-(dimethylamino)pyrazolo[1,5-a]-
pyridin-2-yloxy)ethyl]-1-methyl-3H-imidazol-1-ium
salt

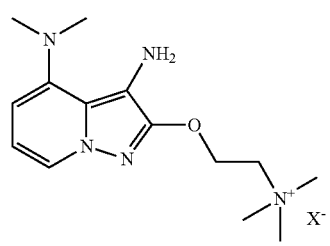

[2-(3-Amino-4-(dimethylamino)pyra-
zolo[1,5-a]-pyridin-2-yloxy)ethyl]tri-
methylammonium salt -continued

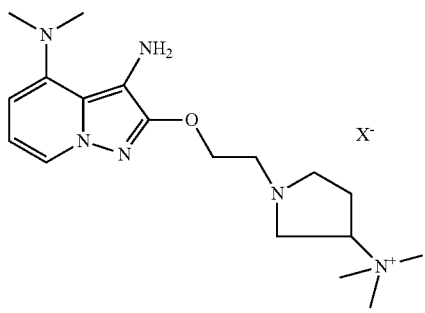

{1-[2-(3-Amino-4-dimethylamino)pyrazolo[1,5-a]-
pyridin-2-yloxy)ethyl]pyrrolidin-3-
yl}trimethylammonium salt

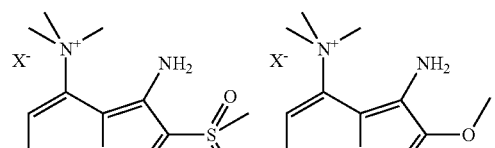

(3-Amino-2-(methanesul-
phonyl)pyrazolo[1,5-a]-
pyridin-4-yl)trimethylammon-
ium salt (3-Amino-2-(methoxy-
pyrazolo[1,5-a]pyridin-4-
yl)trimethylammonium
salt their addition salts, their solvates and the solvates of their salts.

The nature of the counterion is not determining for the dyeing power of the compounds of formula (II).

When $R'_1$, or $R'_2$ denote a heterocycle, this heterocycle is preferably a cationic heterocycle or a heterocycle substituted by a cationic radical. Mention may be made, by way of example, of imidazoles substituted by a quaternary ammonium radical or imidazoliums, piperazines substituted by a quaternary ammonium radical or piperaziniums, pyrrolidines substituted by a quaternary ammonium radical or pyrrolidiniums, or diazepanes substituted by a quaternary ammonium radical or diazepaniums.

According to a different embodiment, $R'_1$, or $R'_2$ represent an $-N^+R_{17}R_{18}R_{19}$ group, $R_{17}$, $R_{18}$ and $R_{19}$ being linear or branched $C_1$-$C_5$ alkyls which are optionally substituted by one or more hydroxyl groups, such as trialkylammonium, tri(hydroxyalkyl)ammonium, (hydroxyalkyl)dialkylammonium or di(hydroxyalkyl)alkylammonium.

The $R'_3$, $R'_4$ and $R'_5$ radicals can independently be a hydrogen atom or an optionally substituted $C_1$-$C_4$ alkyl radical. Mention may be made, by way of example, of the methyl, ethyl, hydroxyethyl, aminoethyl, propyl or butyl radicals. According to a specific embodiment, $R'_3$, $R'_4$ and $R'_5$ independently represent a hydrogen atom or a $C_1$-$C_4$ alkyl radical.

According to a specific embodiment, $R'_4$ and $R'_5$ together form a partially saturated or unsaturated 5- or 6-membered ring, in particular a cyclopentene or cyclohexene, which is optionally substituted.

According to a specific embodiment, the compound of formula (II) corresponds to the following formula (II'):

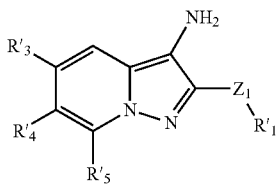

(II')

in which $Z_1$, $R'_1$, $R'_3$, $R'_4$ and $R'_5$ are as defined above.

According to a specific embodiment of this formula, $Z_1$ represents a covalent bond, an —$NR'_6(CH_2)_q$— radical or an —$O(CH_2)_p$— radical and $R'_1$, is a cationic radical.

Preference is very particularly given, as cationic oxidation bases of formula (II), to the following bases:

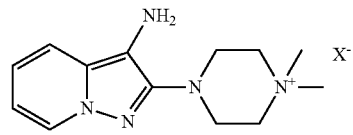

4-(3-aminopyrazolo[1,5-a]pyridin-2-yl)-1,1-dimethylpiperazin-1-ium salt

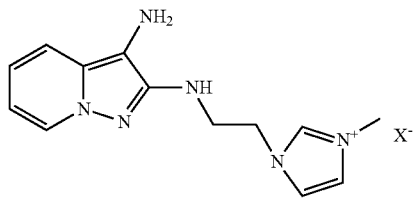

3-[2-(3-aminopyrazolo[1,5-a]pyridin-2-ylamino)ethyl]-1-methyl-3H-imidazol-1-ium salt their addition salts, their solvates and the solvates of their salts.

The composition according to the invention comprises at least one coupler, such as those which are conventionally used for the dyeing of keratinous fibres.

Mention may in particular be made, among these couplers, of meta-phenylenediamines, meta-aminophenols, meta-diphenols, naphthalene couplers, heterocyclic couplers and their addition salts, their solvates and the solvates of their salts.

Mention may be made, by way of example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxy-benzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-di hydroxy-4-methylpyridine, 1-H-3-methylpyrazole-5-one, 1-phenyl-3-methylpyrazole-5-one, 2,6-dimethylpyrazolo[1,5-b]1,2,4-triazole, 2,6-dimethylpyrazolo[3,2-c]1,2,4-triazole, 6-methylpyrazolo[1,5-a]benzimidazole, their addition salts with an acid, their solvates and the solvates of their salts, and their mixtures.

The composition according to the invention can comprise at least one additional oxidation base other than the compounds of formulae (I) and (II) as defined above, their addition salts, their solvates and the solvates of their salts.

By way of example, the oxidation bases are chosen from para-phenylenediamines, bisphenylalkylenediamines, para-aminophenols, ortho-aminophenols, heterocyclic bases, their addition salts, their solvates and the solvates of their salts.

Mention may be made, among para-phenylenediamines, by way of example, of para-phenylenediamine, para-toluoylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-di-methyl-para-phenylenediamine, N,N-diethyl-para-phenylenediamine, N,N-dipropyl-para-phenylenediamine, 4-amino-N,N-diethyl-3-methylaniline, N,N-bis-(β-hydroxy-ethyl)-para-phenylenediamine, 4-N,N-bis(β-hydroxyethyl)amino 2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-amino-toluene, 3-hydroxy-1-(4'-aminophenyl)pyrrolidine, their addition salts with an acid, their solvates and the solvates of their salts.

Among the para-phenylenediamines mentioned above, para-phenylenediamine, para-toluoylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, their addition salts with an acid, their solvates and the solvates of their salts are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine, 1,8-bis(2,5-diaminophenoxy)-3,6-dioxaoctane, their addition salts, their solvates and the solvates of their salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(amino-methyl)phenol, 4-amino-2-

[(β-hydroxyethyl)aminomethyl]phenol, 4-amino-2-fluorophenol, their addition salts with an acid, their solvates and the solvates of their salts.

Mention may be made, among ortho-aminophenols, by way of example, of 2-aminophenol, 2-amino-5-methylphenol, 2-amino-6-methylphenol, 5-acetamido-2-aminophenol, their addition salts, their solvates and the solvates of their salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-[(4-methoxyphenyl)amino]-3-aminopyridine, 3,4-diaminopyridine, their addition salts, their solvates and the solvates of their salts.

Mention may be made, among pyrimidine derivatives, of the compounds described, for example, in Patents DE 2 359 399; JP 88-169571; JP 05-63124; EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, their addition salts, their solvates and the solvates of their salts.

Mention may be made, among pyrazole derivatives, of the compounds described in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, their addition salts, their solvates and the solvates of their salts. Use may also be made of 4,5-diamino-1-(β-methoxyethyl)pyrazole.

Use will preferably be made of a 4,5-diaminopyrazole and more preferably still of 4,5-diamino-1-(β-hydroxyethyl)pyrazole and/or one of its salts and/or their solvates and the solvates of their salts.

Mention may also be made, as pyrazole derivatives, of diamino-N,N-dihydropyrazolopyrazolones, in particular those described in Application FR-A-2 886 136, such as the following compounds, their addition salts, their solvates and the solvates of their salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-[3-(dimethylamino)pyrrolidin-1-yl]-1,2-diethyl-1,2-dihydropyrazol-3-one or 2,3-diamino-6-hydroxy-6,7-dihydro-1H,5H-pyrazolo-[1,2-a]pyrazol-1-one.

It will be preferable to use 2,3-diamino-6,7-dihydro-1H,5H-pyrazolo[1,2-a]pyrazol-1-one and/or one of its salts and/or their solvates and the solvates of their salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts and/or their solvates and/or the solvates of their salts.

The addition salts of the oxidation bases and couplers are chosen in particular from the addition salts with an acid, such as hydrochlorodes, hydrobromides, sulphates, citrates, succinates, tartrates, lactates, tosylates, benzenesulphonates, phosphates and acetates.

The oxidation base or bases each advantageously represent from 0.001 to 10% by weight, with respect to the total weight of the composition, preferably from 0.005 to 6% by weight, with respect to the total weight of the composition, and more preferably still from 0.05 to 1.5% by weight, with respect to the total weight of the composition.

The content of coupler(s) each advantageously represents from 0.001 to 10% by weight, with respect to the total weight of the composition, preferably from 0.005 to 6% by weight, with respect to the total weight of the composition, and more preferably still from 0.05 to 1.5% by weight, with respect to the total weight of the composition.

The composition in accordance with the invention can also provide at least one direct dye.

The direct dyes that may be used are, for example, synthetic or natural dyes, chosen from ionic or nonionic entities, preferably cationic or nonionic entities.

The dyeing composition in accordance with the invention can additionally comprise at least one direct dye which can be chosen in particular from nitrobenzene dyes, azo direct dyes or methine direct dyes. These direct dyes may be of nonionic, anionic or cationic nature.

When they are present, the direct dye or dyes more particularly represent from 0.0001 to 10% by weight of the total weight of the composition and preferably from 0.005 to 5% by weight.

The composition according to the invention also comprises at least one oxidizing agent.

The oxidizing agent or agents are, for example, chosen from hydrogen peroxide, urea hydrogen peroxide, alkali metal bromates or ferricyanides, peroxygenated salts, such as, for example, persulphates or perborates, peracids and their precursors, and alkali metal or alkaline earth metal percarbonates.

Preferably, the oxidizing agent is not chosen from peroxygenated salts.

Advantageously, the oxidizing agent is hydrogen peroxide.

The content of oxidizing agent(s) more particularly represents from 0.1 to 20% by weight, preferably from 0.5 to 10% by weight, with respect to the weight of the composition.

According to a specific embodiment of the invention, the composition comprises at least one basifying agent. This agent may be chosen from inorganic or organic or hybrid alkaline agents, or mixtures thereof.

The inorganic alkaline agent or agents are preferably chosen from aqueous ammonia, alkaline carbonates or bicarbonates such as sodium or potassium carbonates and sodium or potassium bicarbonates, sodium hydroxide or potassium hydroxide, or mixtures thereof.

The organic alkaline agent or agents are preferably chosen from organic amines with a $pK_b$ at 25° C. of less than 12, preferably less than 10 and even more advantageously less than 6. It should be noted that it is the $pK_b$ corresponding to the functional group of highest basicity.

Hybrid compounds that may be mentioned include the salts of the amines mentioned previously with acids such as carbonic acid or hydrochloric acid.

The organic alkaline agent or agents are, for example, chosen from alkanolamines, oxyethylenated and/or oxypropylenated ethylenediamines, amino acids and the compounds of following formula (III):

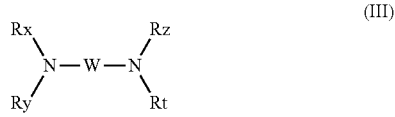

in which W is a $C_1$-$C_6$ alkylene residue optionally substituted by a hydroxyl group or a $C_1$-$C_6$ alkyl radical and Rx, Ry, Rz and Rt, which are identical or different, represent a hydrogen atom, a $C_1$-$C_6$ alkyl radical, a $C_1$-$C_6$ hydroxyalkyl radical or a $C_1$-$C_6$ aminoalkyl radical.

Mention may be made, as an example of such amines, of 1,3-diaminopropane, 1,3-diamino-2-propanol, spermine or spermidine.

The term "alkanolamine" is understood to mean an organic amine comprising a primary, secondary or tertiary amine functional group and one or more linear or branched $C_1$-$C_8$ alkyl groups carrying one or more hydroxyl radicals.

Alkanolamines, such as mono-, di- or trialkanolamines, comprising from one to three identical or different $C_1$-$C_4$ hydroxyalkyl radicals are suitable in particular for the implementation of the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids which can be used are of natural or synthetic origin, in their L, D or racemic form, and comprise at least one acid functional group chosen more particularly from carboxylic acid, sulphonic acid, phosphonic acid or phosphoric acid functional groups. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine functional group optionally included in a ring or in a ureido functional group.

Such basic amino acids are preferably chosen from those corresponding to the following formula (IV):

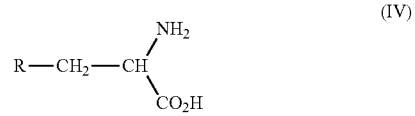

in which R denotes a group chosen from:

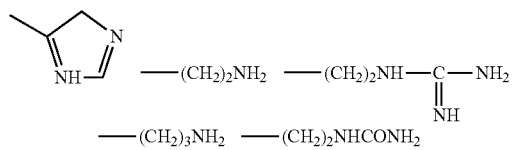

The compounds corresponding to the formula (IV) are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine is chosen from compounds comprising a guanidine functional group. As amines of this type that may be used in the present invention, besides arginine that has already been mentioned as an amino acid, mention may be made especially of creatine, creatinine, 1,1-dimethylguanidine, 1,1-diethyl-guanidine, glycocyamine, metformin, agmatine, N-amidinoalanine, 3-guanidinopropionic acid, 4-guanidinobutyric acid and 2-([amino(imino)-methyl]amino)ethane-1-sulphonic acid.

Mention may be made in particular of the use of guanidine carbonate or monoethanolamine hydrochloride as hybrid compounds.

The composition of the invention preferably comprises one or more alkanolamines and/or one or more basic amino acids, more advantageously one or more alkanolamines. More preferentially still, the organic amine is monoethanolamine.

Advantageously, the composition according to the invention exhibits a content of alkaline agent(s), if it is (they are) present, ranging from 0.01 to 30% by weight and preferably from 0.1 to 20% by weight, with respect to the weight of the said composition.

The composition can also include various adjuvants conventionally used in compositions for dyeing or lightening the hair, such as anionic, cationic or nonionic surfactants or their mixtures; thickeners; anionic, cationic or nonionic polymers or their mixtures; antioxidants; penetration agents; sequestering agents; fragrances; dispersing agents; film-forming agents; ceramides; preservatives; or opacifying agents.

The above adjuvants are generally present in amounts of, for each of them, between 0.01 and 20% by weight, with respect to the weight of the composition.

The composition according to the invention can comprise water and/or at least one organic solvent.

Mention may be made, as organic solvent, for example, of linear or branched monoalcohols or diols which are preferably saturated and which comprise from 2 to 10 carbon atoms, such as ethyl alcohol, isopropyl alcohol, hexylene glycol (2-methyl-2,4-pentanediol), neopentyl glycol, 3-methyl-1,5- pentanediol, butylene glycol, dipropylene glycol and propylene glycol; aromatic alcohols, such as benzyl alcohol or phenylethyl alcohol; polyols comprising more than two hydroxyl functional groups, such as glycerol; or polyol ethers, such as, for example, ethylene glycol monomethyl, monoethyl and monobutyl ethers, propylene glycol or its ethers, such as, for example, propylene glycol monomethyl ether, and diethylene glycol alkyl ethers, in particular $C_1$-$C_4$ ethers, such as, for example, diethylene glycol monoethyl ether or monobutyl ether, alone or as a mixture.

The organic solvents, when they are present, generally represent between 1% and 40% by weight relative to the total weight of the dyeing composition, and preferably between 5% and 30% by weight relative to the total weight of the dyeing composition.

Preferably, the composition of the invention comprises water, for example between 10 and 70%, better still from 20 to 55%, of the total weight of the composition.

The dyeing composition according to the invention may be in various forms, such as in the form of liquids, creams or gels, or in any other form that is suitable for dyeing keratinous fibres, and especially human hair.

Advantageously, the composition according to the invention is in the form of a gel or a cream.

The pH of the composition according to the invention is generally between 3 and 12, preferably between 5 and 11 and preferentially between 7 and 11, limits included.

It may be adjusted to the desired value by means of acidifying or basifying agents normally used in the dyeing of keratinous fibres.

The basifying agents are, for example, those described previously.

Examples of acidifying agents that may be mentioned include inorganic or organic acids, for instance hydrochloric acid, orthophosphoric acid, carboxylic acids, for instance tartaric acid, citric acid or lactic acid, or sulphonic acids.

The composition of the invention may be obtained by mixing at least two or even three different compositions, or optionally more than three different compositions. One or more of the compositions leading, by mixing, to the composition of the invention may be anhydrous. It should be noted that the composition according to the invention is prepared just before being applied to the human keratinous fibres.

According to a first alternative form, the composition according to the invention is obtained by mixing a first composition comprising at least one fatty substance, at least one specific pyrazolopyridine oxidation base and at least one coupler with a second composition comprising at least one oxidizing agent.

According to a second alternative form of the invention, the composition according to the invention is obtained by mixing a first composition comprising at least one fatty substance, a second composition comprising at least one specific pyrazolopyridine oxidation base and at least one coupler, and a third composition comprising at least one oxidizing agent.

The ingredients of the abovementioned compositions and the contents thereof are determined as a function of the characteristics detailed previously for the final composition according to the invention.

In each of the abovementioned alternative forms, the oxidizing composition is preferably an aqueous composition. In particular, it comprises more than 5% by weight of water, preferably more than 10% by weight of water and even more advantageously more than 20% by weight of water.

It may also comprise one or more organic solvents chosen from those listed previously; these solvents more particularly representing, when they are present, from 1% to 40% by weight and preferably from 5% to 30% by weight relative to the weight of the oxidizing composition.

The oxidizing composition also preferably comprises one or more acidifying agents. Among the acidifying agents, examples that may be mentioned include inorganic or organic acids, for instance hydrochloric acid, orthophosphoric acid, sulphuric acid, carboxylic acids, for instance acetic acid, tartaric acid, citric acid or lactic acid, and sulphonic acids.

Usually, the pH of the oxidizing composition, when it is aqueous, is less than 7.

Preferably, the oxidizing composition comprises hydrogen peroxide as oxidizing agent, in aqueous solution, the concentration of which varies, more particularly, from 0.1% to 50%, more particularly between 0.5% and 20% and more preferably still between 1% and 15% by weight relative to the weight of the oxidizing composition.

The dyeing method according to the invention thus consists in applying the composition according to the invention to dry or wet human keratinous fibres. The temperature during the method is conventionally between ambient temperature (between 15 and 25° C.) and 80° C., preferably between ambient temperature and 60° C.

After a leave-in time of from one minute to one hour, preferably from 5 minutes to 30 minutes, the keratinous fibres are optionally rinsed with water and are optionally washed with a shampoo followed by rinsing with water, before being dried or allowed to dry.

The invention also relates to a two-compartment device including, in one, a first composition comprising at least one fatty substance, at least one specific pyrazolopyridine oxidation base and at least one coupler and, in the other, a second composition comprising at least one oxidizing agent, the compositions of the compartments being intended to be mixed to give the composition according to the invention, immediately before application to human keratinous fibres.

Finally, the invention relates to a three-compartment device including, in one, a first composition comprising at least one fatty substance, in another, a second composition comprising at least one specific pyrazolopyridine oxidation base and at least one coupler and, in the last, a third composition comprising at least one oxidizing agent, the compositions of the three compartments being intended to be mixed to give the composition according to the invention, immediately before application to human keratinous fibres.

The following examples serve to illustrate the invention without, however, exhibiting a limiting nature.

EXAMPLES

Example 1

The following three compositions are prepared.

|  | Composition 1 |
|---|---|
| Disteardimonium hectorite | 3 g |
| Octyldodecanol | 11.5 g |
| Glycol distearate | 8 g |
| Liquid petrolatum | 64.5 g |
| Propylene carbonate | 1 g |
| Laureth-2 | 1 g |
| Polysorbate 21 | 11 g |

|  | Composition 2 |
| --- | --- |
| Sequestering agent | 1 g |
| Reducing agent | 0.7 g |
| Monoethanolamine | 14.5 g |
| 2-[(3-Aminopyrazolo[1,5-a]pyridin-2-yl)oxy]ethanol hydrochloride | 3.4 g |
| 5-Amino-6-chloro-2-methylphenol | 2.3 g |
| Natrosol 250 HHR (hydroxyethylcellulose) | 1.5 g |
| Hexylene glycol | 3 g |
| Dipropylene glycol | 3 g |
| Denatured absolute ethyl alcohol | 8.25 g |
| Deionized water | q.s. 100 g |
| Propylene glycol | 6.2 g |
| Antioxidant | 0.25 g |

|  | Composition 3 |
| --- | --- |
| Sequestering agent | 0.15 g |
| Hydrogen peroxide as a 50% aqueous solution (200-vol aqueous hydrogen peroxide solution) | 12 g |
| Sodium stannate | 0.04 g |
| Phosphoric acid at 85% by weight in water | q.s. pH 2.2 |
| Tetrasodium pyrophosphate decahydrate | 0.03 g |
| Liquid petrolatum | 20 g |
| Poly[(dimethyliminio)-1,3-propanediyl(dimethyliminio)-1,6-hexanediyl dichloride] as an aqueous solution at 60% by weight | 0.25 g |
| Polyquaternium-6 | 0.5 g |
| Deionized water | q.s. 100 g |
| Glycerol | 0.5 g |
| Cetearyl alcohol ($C_{16}/C_{18}$ 30/70) | 8 g |
| Ceteareth-33 | 3 g |
| Protected oxyethylenated (4 EO) rapeseed acid amide | 1.3 g |
| Vitamin E | 0.1 g |

The 3 compositions are mixed at the time of use in the following proportions: 10 g of composition 1+4 g of composition 2+16 g of composition 3, and the mixture thus obtained is applied to locks of grey hair comprising 90% of natural white hairs at the rate of 10 g of mixture per 1 g of hair for 30 minutes at ambient temperature. The hair is then rinsed, washed with a standard shampoo and dried.

The hair colouring is evaluated visually.

|  | Height of tone | Highlight |
| --- | --- | --- |
| Example 1 | Chestnut | Coppery red |

Example 2

The following three compositions are prepared.

|  | Composition 1 |
| --- | --- |
| Disteardimonium hectorite | 3 g |
| Octyldodecanol | 11.5 g |
| Glycol distearate | 8 g |
| Liquid petrolatum | 64.5 g |
| Propylene carbonate | 1 g |
| Laureth-2 | 1 g |
| Polysorbate 21 | 11 g |

|  | Composition 2 |
| --- | --- |
| Sequestering agent | 1 g |
| Reducing agent | 0.7 g |
| Monoethanolamine | 14.5 g |
| 4-(3-Aminopyrazolo[1,5-a]pyridin-2-yl)-1,1-dimethylpiperazin-1-ium chloride hydrochloride | 4.8 g |
| 1-(β-Hydroxyethyloxy)-2,4-diaminobenzene dihydrochloride | 3.6 g |
| Natrosol 250 HHR (hydroxyethylcellulose) | 1.5 g |
| Hexylene glycol | 3 g |
| Dipropylene glycol | 3 g |
| Denatured absolute ethyl alcohol | 8.25 g |
| Deionized water | q.s. 100 g |
| Propylene glycol | 6.2 g |
| Antioxidant | 0.25 g |

|  | Composition 3 |
| --- | --- |
| Sequestering agent | 0.15 g |
| Hydrogen peroxide as a 50% aqueous solution (200-vol aqueous hydrogen peroxide solution) | 12 g |
| Sodium stannate | 0.04 g |
| Phosphoric acid at 85% by weight in water | q.s. pH 2.2 |
| Tetrasodium pyrophosphate decahydrate | 0.03 g |
| Liquid petrolatum | 20 g |
| Poly[(dimethyliminio)-1,3-propanediyl(dimethyliminio)-1,6-hexanediyl dichloride] as an aqueous solution at 60% by weight | 0.25 g |
| Polyquaternium-6 | 0.5 g |
| Deionized water | q.s. 100 g |
| Glycerol | 0.5 g |
| Cetearyl alcohol ($C_{16}/C_{18}$ 30/70) | 8 g |
| Ceteareth-33 | 3 g |
| Protected oxyethylenated (4 EO) rapeseed acid amide | 1.3 g |
| Vitamin E | 0.1 g |

The 3 compositions are mixed at the time of use in the following proportions: 10 g of composition 1+4 g of composition 2+16 g of composition 3, and the mixture thus obtained is applied to locks of grey hair comprising 90% of natural white hairs in a proportion of 10 g of mixture per 1 g of hair for 30 minutes at ambient temperature. The hair is then rinsed, washed with a standard shampoo and dried.

The hair colouring is evaluated visually.

|  | Height of tone | Highlight |
| --- | --- | --- |
| Example 2 | Chestnut | Vivid blue |

Example 3

The following three compositions are prepared.

|  | Composition 1 |
| --- | --- |
| Disteardimonium hectorite | 3 g |
| Octyldodecanol | 11.5 g |
| Glycol distearate | 8 g |
| Liquid petrolatum | 64.5 g |
| Propylene carbonate | 1 g |
| Laureth-2 | 1 g |
| Polysorbate 21 | 11 g |

| | Composition 2 |
|---|---|
| Sequestering agent | 1 g |
| Reducing agent | 0.7 g |
| Monoethanolamine | 14.5 g |
| 1-{2-[(3-Aminopyrazolo[1,5-a]pyridin-2-yl)amino]-ethyl}-3-methyl-1H-imidazol-3-ium chloride hydrochloride | 3.3 g |
| 1-Methyl-2-hydroxy-4-(β-hydroxyethylamino)-benzene | 1.67 g |
| Natrosol 250 HHR (hydroxyethylcellulose) | 1.5 g |
| Hexylene glycol | 3 g |
| Dipropylene glycol | 3 g |
| Denatured absolute ethyl alcohol | 8.25 g |
| Deionized water | q.s. 100 g |
| Propylene glycol | 6.2 g |
| Antioxidant | 0.25 g |

| | Composition 3 |
|---|---|
| Sequestering agent | 0.15 g |
| Hydrogen peroxide as a 50% aqueous solution (200-vol aqueous hydrogen peroxide solution) | 12 g |
| Sodium stannate | 0.04 g |
| Phosphoric acid at 85% by weight in water | q.s. pH 2.2 |
| Tetrasodium pyrophosphate decahydrate | 0.03 g |
| Liquid petrolatum | 20 g |
| Poly[(dimethyliminio)-1,3-propanediyl(dimethyliminio)-1,6-hexanediyl dichloride] as an aqueous solution at 60% by weight | 0.25 g |
| Polyquaternium-6 | 0.5 g |
| Deionized water | q.s. 100 g |
| Glycerol | 0.5 g |
| Cetearyl alcohol ($C_{16}/C_{18}$ 30/70) | 8 g |
| Ceteareth-33 | 3 g |
| Protected oxyethylenated (4 EO) rapeseed acid amide | 1.3 g |
| Vitamin E | 0.1 g |

The 3 compositions are mixed at the time of use in the following proportions: 10 g of composition 1+4 g of composition 2+16 g of composition 3, and the mixture thus obtained is applied to locks of grey hair comprising 90% of natural white hairs in a proportion of 10 g of mixture per 1 g of hair for 30 minutes at ambient temperature. The hair is then rinsed, washed with a standard shampoo and dried.

The hair colouring is evaluated visually.

| | Height of tone | Highlight |
|---|---|---|
| Example 3 | Chestnut | Vivid purple |

The invention claimed is:

1. A composition for dyeing keratinous fibers comprising:
   a) at least about 25% by weight of at least one fatty substance, wherein said at least one fatty substance does not comprise a carboxylic acid functional group;
   b) at least one aminopyrazolopyridine oxidation base chosen from bases of formula (I), bases of formula (II), and the addition salts, solvates and solvates of the salts thereof:

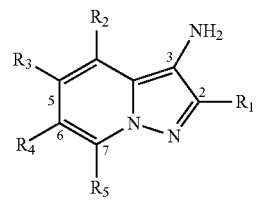

(I)

wherein:
$R_1$, $R_2$, $R_3$, $R_4$ and $R_5$, which are identical or different, are chosen from hydrogen atoms; halogen atoms; —$NHSO_3H$ radicals; hydroxyl radicals; ($C_1$-$C_4$)alkyl radicals; ($C_1$-$C_4$)alkoxy radicals; ($C_1$-$C_4$)alkylthio radicals; mono($C_1$-$C_4$)alkylamino radicals; di($C_1$-$C_4$)alkylamino radicals wherein the two alkyl groups can, in conjunction with the nitrogen atom to which they are bonded, form a ring which is optionally interrupted by at least one atom chosen from nitrogen, oxygen and sulphur atoms; heterocycles; nitro radicals; phenyl radicals; carbonyl radicals; alkoxy($C_1$-$C_4$)carbonyl radicals; carboxamido radicals; cyano radicals; amino radicals; sulphonyl radicals; —$CO_2H$ radicals; —$SO_3H$ radicals; —$PO_3H_2$ radicals; —$PO_4H_2$ radical; and groups

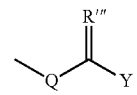

wherein R''' is chosen from oxygen and nitrogen atoms, Q is chosen from oxygen atoms, NH groups, and NH($C_1$-$C_4$)alkyl groups, and Y is chosen from hydroxyl, amino, ($C_1$-$C_4$)alkyl, ($C_1$-$C_4$)alkoxy, ($C_1$-$C_4$)alkylamino and di($C_1$-$C_4$)alkylamino radicals;

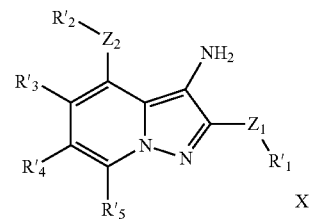

(II)

wherein:
$Z_1$ and $Z_2$, which may be identical or different, are chosen from single covalent bonds and divalent radicals chosen from:
—$O(CH_2)_p$— radicals, wherein p is an integer ranging from 0 to 6; and
—$NR'_6(CH_2)_q(C_6H_4)_t$— radicals, wherein q is an integer ranging from 0 to 6, t is chosen from 0 and 1, and $R'_6$ is chosen from hydrogen atoms and $C_1$-$C_6$ alkyl radicals optionally substituted by at least one hydroxyl group;
$Z_1$ may also be chosen from divalent radicals —S—, —SO— and —$SO_2$— when $R'_1$ is a methyl radical;
$R'_1$ and $R'_2$, which may be identical or different, are chosen from
hydrogen atoms;
$C_1$-$C_{10}$ alkyl radicals, optionally substituted and optionally interrupted by a group chosen from heteroatoms, O, N, Si, S, SO and $SO_2$;

halogen atoms;

SO$_3$H radicals;

substituted and unsubstituted and saturated, unsaturated and aromatic 5- to 8-membered rings optionally including at least one group chosen from heteroatoms, N, O, S, SO$_2$ and —CO—, wherein the ring may be at least one of cationic and substituted by a cationic radical;

—N$^+$R$_{17}$R$_{18}$R$_{19}$ groups, wherein R$_{17}$, R$_{18}$ and R$_{19}$ are chosen from linear and branched C$_1$-C$_5$ alkyls optionally substituted by at least one hydroxyl group;

when Z$_1$ or Z$_2$ respectively represents a covalent bond, then R'$_1$ or R'$_2$ can respectively be chosen from optionally substituted C$_1$-C$_6$ alkylcarbonyl radicals;

—O—CO—R, —CO—O—R, NR—CO—R' and —CO—NRR' radicals wherein R and R', which may be identical or different, are chosen from hydrogen atoms and optionally substituted C$_1$-C$_6$ alkyl radicals;

R'$_3$, R'$_4$ and R'$_5$, which may be identical or different, are chosen from hydrogen atoms;

hydroxyl radicals;

C$_1$-C$_6$ alkoxy radicals;

C$_1$-C$_6$ alkylthio radicals;

amino radicals;

monoalkylamino radicals;

di(C$_1$-C$_6$) alkylamino radicals wherein the alkyl radicals can form, with the nitrogen atom to which they are attached, an optionally saturated and optionally aromatic 5- to 8-membered heterocycle which can include at least one group chosen from heteroatoms, N, O, S, SO$_2$ and CO, it being possible for the heterocycle to be at least one of cationic and substituted by a cationic radical;

optionally substituted C$_1$-C$_6$ alkylcarbonyl radicals;

—O—CO-R, —OO—O—R, NR—CO—R' and —CO—NRR' radicals wherein R and R', which may be identical or different, are chosen from hydrogen atoms and optionally substituted C$_1$-C$_6$ alkyl radicals;

halogen atoms;

—NHSO$_3$H radicals;

optionally substituted C$_1$-C$_4$ alkyl radicals;

saturated, unsaturated and aromatic carbon rings which are optionally substituted;

R'$_3$, R'$_4$ and R'$_5$ can form, in pairs, a ring which is optionally partially saturated;

X is chosen from ions and groups of ions which makes it possible to provide the electrical neutrality of the derivative of formula (II);

wherein at least one of the groups R'$_1$ and R'$_2$ is a cationic radical;

c) at least one coupler; and d) at least one oxidizing agent.

2. The composition according to claim 1, wherein the at least one fatty substance not comprising a carboxylic acid functional group is chosen from lower C$_6$-C$_{16}$ alkanes, animal non-silicone oils, vegetable non-silicone oils, synthetic non-silicone oils, mineral hydrocarbons, synthetic hydrocarbons, fatty alcohols, fatty acid esters, fatty alcohol esters, non-silicone waxes and silicones.

3. The composition according to claim 1, wherein the at least one fatty substance not comprising a carboxylic acid functional group is chosen from compounds that are liquid at ambient temperature and at atmospheric pressure and compounds that are pasty at ambient temperature and at atmospheric pressure.

4. The composition according claim 1, wherein the at least one fatty substance not comprising a carboxylic acid functional group is chosen from lower C$_6$-C$_{16}$ alkanes, non-silicone vegetable oils, non-silicone synthetic oils, mineral hydrocarbons, synthetic hydrocarbons, fatty alcohols, fatty acid esters, and fatty alcohol esters.

5. The composition according to claim 1, wherein the at least one fatty substance not comprising a carboxylic acid functional group is chosen from liquid petrolatum, polydecenes, liquid fatty acid esters, fatty alcohol esters, and liquid fatty alcohols.

6. The composition according to claim 1, wherein the bases of formula (I) are chosen from the compounds of formula:

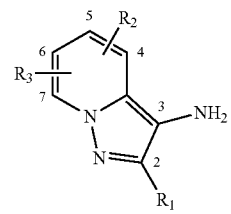

wherein:

R$_1$, R$_2$, R$_3$, which are identical or different, are chosen from hydrogen atoms; halogen atoms; hydroxyl radicals; (C$_1$-C$_4$)alkyl radicals; (C$_1$-C$_4$)alkylthio radicals; (C$_1$-C$_4$) alkoxy radicals; —NHSO$_3$H radicals; amino radicals; (C$_1$-C$_4$)alkylamino radicals;

di(C$_1$-C$_4$)alkylamino radicals wherein the two alkyl groups can form, together with the nitrogen atom to which they are bonded, a ring that is optionalled interrupted by at least one atom chosen from nitrogen, oxygen and sulphur atoms; heterocycles; sulphonamido radicals; carbonyl radicals; (C$_1$-C$_4$)alkoxycarbonyl radicals; carboxamido radicals; and groups of formula:

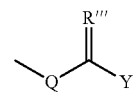

wherein R''' is chosen from oxygen and nitrogen atoms, Q is chosen from oxygen atoms, NH groups, and NH(C$_1$-C$_4$)alkyl groups, and Y is chosen from hydroxyl, amino, C$_1$-C$_4$ alkyl, (C$_1$-C$_4$)alkoxy, (C$_1$-C$_4$)alkylamino and di(C$_1$-C$_4$)alkylamino radicals.

7. The composition according to claim 1, wherein the bases of formula (I) are chosen from:

pyrazolo[1,5-a]pyridin-3-ylamine;
2-(acetylamino)pyrazolo[1,5-a]pyridin-3-ylamine;
2-(morpholin-4-yl)pyrazolo[1,5-a]pyridin-3-ylamine;
3-aminopyrazolo[1,5-a]pyridine-2-carboxylic acid;
2-methoxypyrazolo[1,5-a]pyridin-3-ylamine;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-(morpholin-4-yl)pyrazolo[1,5-a]pyridin-3-ylamine;
pyrazolo[1,5-a]pyridine-3,5-diamine;
5-(morpholin-4-yl)pyrazolo[1,5-a]pyridin-3-ylamine;
2-[(3-aminopyrazolo[1,5-a]pyridin-5-yl)(2-hydroxyethyl) amino]ethanol;

2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-amino-pyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-(pyridin-3-yl)ethyl)pyrazolo[1,5-a]pyridine-2,3-diamine; and
the addition salts, solvates, and the solvates of the salts thereof.

8. The composition according to claim 1, wherein, in formula (II), at least one of $Z_1$ and $Z_2$ is chosen from covalent bonds, $-NR'_6(CH_2)_q-$ radicals and
$-O(CH_2)_p-$ radicals, and at least one of $R'_1$ and $R'_2$ is a cationic radical.

9. The composition according to claim 1, wherein in formula (II), at least one of $R'_1$ and $R'_2$ is chosen from imidazoles substituted by a quaternary ammonium radical, imidazoliums, piperazines substituted by a quaternary ammonium radical, piperaziniums, pyrrolidines substituted by a quaternary ammonium radical, pyrrolidiniums, diazepanes substituted by a quaternium ammonium radical, and diazepaniums.

10. The composition according to claim 1, wherein $R'_1$ and $R'_2$, which may be identical or different, are chosen from hydrogen atoms, trialkylammonium groups, tri(hydroxyalkyl)ammonium groups, (hydroxyalkyl)dialkylammonium groups, and di(hydroxyalkyl)alkylammonium groups.

11. The composition according to claim 1, wherein in formula (II), $R'_3$, $R'_4$ and $R'_5$, which may be identical or different, are chosen from hydrogen atoms and optionally substituted $C_1$-$C_4$ alkyl radicals.

12. The composition according to claim 1, wherein formula (II) is

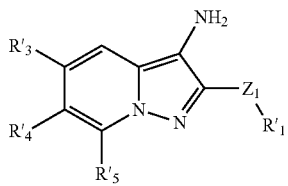

wherein
$Z_1$ is chosen from single covalent bonds, divalent radicals chosen from
$-O(CH_2)_p-$ radicals, wherein p is an integer ranging from 0 to 6;
$-NR'_6(CH_2)_q(C_6H_4)_t-$ radicals, wherein q is an integer ranging from 0 to 6, t is chosen from 0 and 1, and $R'_6$ is chosen from hydrogen atoms and $C_1$-$C_6$ alkyl radicals optionally substituted by at least one hydroxyl group;
$-S-$, $-SO-$, and $-SO_2-$, when $R'_1$ is a methyl radical;
$R'_1$ is chosen from
hydrogen atoms;
$C_1$-$C_{10}$ alkyl radicals, optionally substituted and optionally interrupted by a group chosen from heteroatoms, O, N, Si, S, SO and $SO_2$;
halogen atoms;
$SO_3H$ radicals;
substituted and unsubstituted and saturated, unsaturated and aromatic 5- to 8-membered rings optionally including at least one group chosen from heteroatoms, N, O, S, $SO_2$ and $-CO-$, wherein the ring may be at least one of cationic and substituted by a cationic radical;
$-N^+R_{17}R_{18}R_{19}$ groups, wherein $R_{17}$, $R_{18}$ and $R_{19}$ are chosen from linear and branched $C_1$-$C_5$ alkyls optionally substituted by at least one hydroxyl group;
when $Z_1$ is a covalent bond, then $R'_1$ may be chosen from optionally substituted $C_1$-$C_6$ alkylcarbonyl radicals;
$-O-CO-R$, $-CO-O-R$, $NR-CO-R'$ and $-CO-NRR'$ radicals wherein R and R', which may be identical or different, are chosen from hydrogen atoms and optionally substituted $C_1$-$C_6$ alkyl radicals; and $R'_3$, $R'_4$ and $R'_5$, which may be identical or different, are chosen from
hydrogen atoms;
hydroxyl radicals;
$C_1$-$C_6$ alkoxy radicals;
$C_1$-$C_6$ alkylthio radicals;
amino radicals;
monoalkylamino radicals;
di($C_1$-$C_6$)alkylamino radicals wherein the alkyl radicals can form, with the nitrogen atom to which they are attached, an optionally saturated and optionally aromatic 5- to 8-membered heterocycle which can include at least one group chosen from heteroatoms, N, O, S, $SO_2$ and CO, it being possible for the heterocycle to be at least one of cationic and substituted by a cationic radical;
optionally substituted $C_1$-$C_6$ alkylcarbonyl radicals;
$-O-CO-R$, $-CO-O-R$, $NR-CO-R'$ and $-CO-NRR'$ radicals wherein R and R', which may be identical or different, are chosen from hydrogen atoms and optionally substituted $C_1$-$C_6$ alkyl radicals;
halogen atoms;
$-NHSO_3H$ radicals;
optionally substituted $C_1$-$C_4$ alkyl radicals;
saturated, unsaturated and aromatic carbon rings which are optionally substituted; and
$R'_3$, $R'_4$ and $R'_5$ can form, in pairs, a ring which is optionally partially saturated.

13. The composition according to claim 12 wherein $Z_1$ is chosen from covalent bonds, $-NR'_6(CH_2)_q-$ radicals, and $-O(CH_2)_p-$ radicals, and $R'_1$ is a cationic radical.

14. The composition according to claim 1, wherein the bases of formula (II) are chosen from:

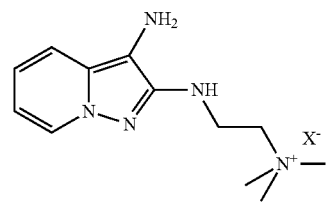

[2-(3-Aminopyrazolo[1,5-a]pyridin-2-ylamino)ethyl]trimethylammonium salt

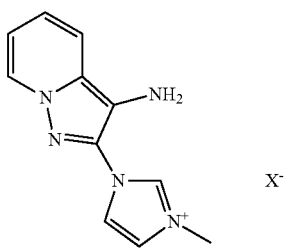

3-(3-Aminopyrazolo[1,5-a]pyridin-
2-yl)-methyl-3H-imidazol-1-ium salt

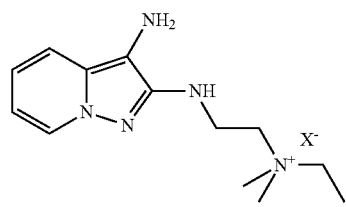

[2-(3-Aminopyrazolo[1,5-a]pyridin-2-
ylamino)ethyl]ethyldimethylammonium salt

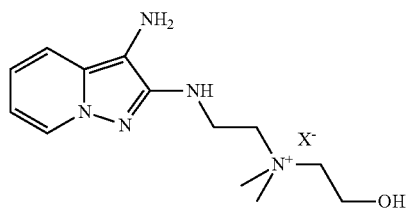

[2-(3-Aminopyrazolo[1,5-a]pyridin-2-
ylamino)ethyl](2-hydroxyethyl)dimethylammonium
salt

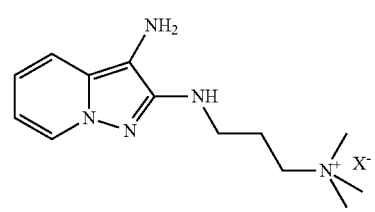

[3-(3-Aminopyrazolo[1,5-a]pyridin-2-
ylamino)propyl]trimethylammonium salt

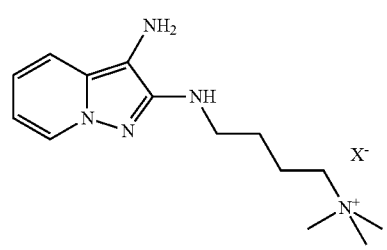

[4-(3-Aminopyrazolo[1,5-a]pyridin-2-
ylamino)butyl]trimethylammonium salt

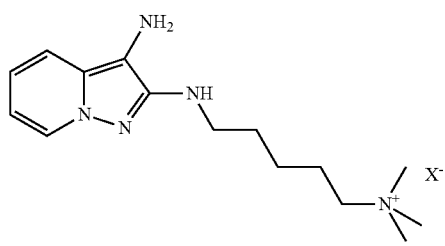

[5-(3-Aminopyrazolo[1,5-a]pyridin-2-
ylamino)pentyl]trimethylammonium salt

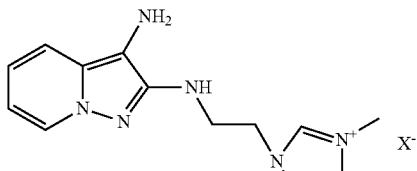

3-[2-(3-Aminopyrazolo[1,5-a]pyridin-2-
ylamino)ethyl]-1-methyl-3H-imidazol-1-ium salt

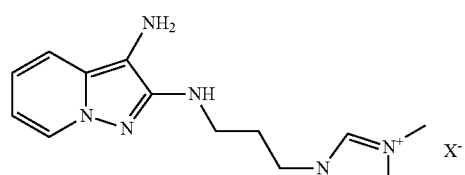

3-[3-(3-Aminopyrazolo[1,5-a]pyridin-2-
ylamino)propyl]-1-methyl-3H-imidazol-1-ium salt

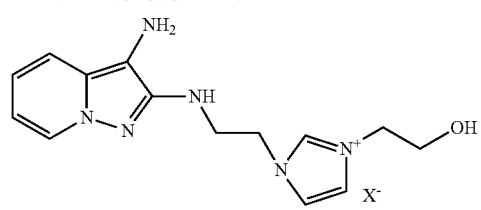

3-[3-(3-Aminopyrazolo[1,5-a]pyridin-2-ylamino)propyl]-1-
(2-hydroxyethyl)-3H-imidazol-1-ium salt

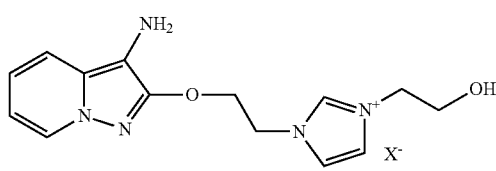

3-[2-(3-Aminopyrazolo[1,5-a]pyridin-2-
yloxy)ethyl]-1-(2-hydroxyethyl)-3H-imidazol-1-ium salt

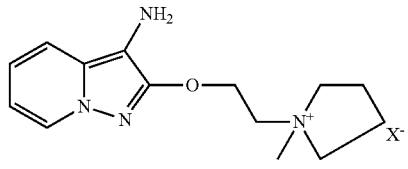

1-{2-[(3-Aminopyrazolo[1,5-a]pyridin-2-
yl)oxy]ethyl}-1-methylpyrrolidinium salt

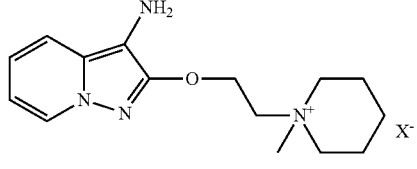

1-{2-[(3-Aminopyrazolo[1,5-a]pyridin-2-
yl)oxy]ethyl}-1-methylpiperdinium salt

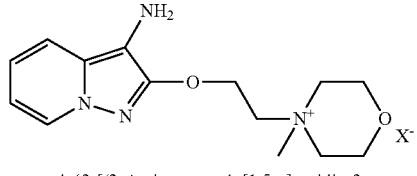

4-{2-[(3-Aminopyrazolo[1,5-a]pyridin-2-
yl)oxy]ethyl}-4-methylmorpholin-4-ium salt -continued

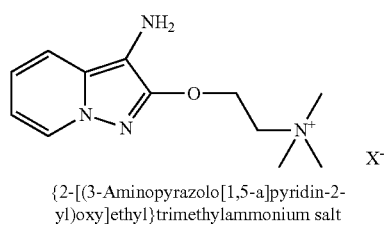

{2-[(3-Aminopyrazolo[1,5-a]pyridin-2-yl)oxy]ethyl}trimethylammonium salt

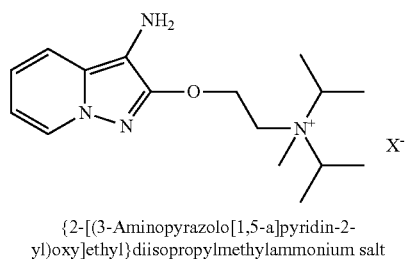

{2-[(3-Aminopyrazolo[1,5-a]pyridin-2-yl)oxy]ethyl}diisopropylmethylammonium salt

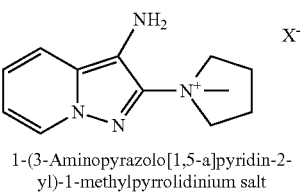

1-(3-Aminopyrazolo[1,5-a]pyridin-2-yl)-1-methylpyrrolidinium salt

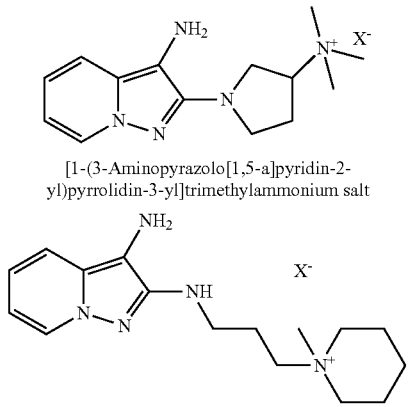

[1-(3-Aminopyrazolo[1,5-a]pyridin-2-yl)pyrrolidin-3-yl]trimethylammonium salt

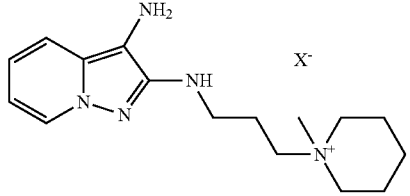

1-[3-(3-Aminopyrazolo[1,5-a]pyridin-2-ylamino)propyl]-1-methylpiperidinium salt

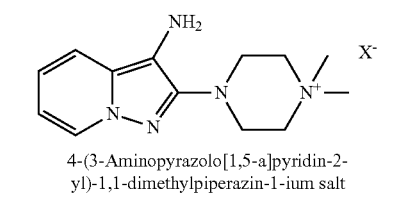

4-(3-Aminopyrazolo[1,5-a]pyridin-2-yl)-1,1-dimethylpiperazin-1-ium salt

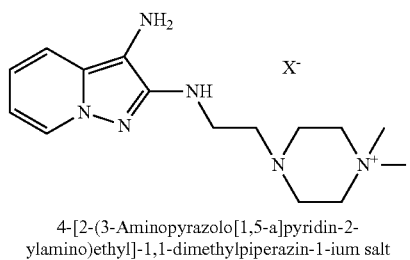

4-[2-(3-Aminopyrazolo[1,5-a]pyridin-2-ylamino)ethyl]-1,1-dimethylpiperazin-1-ium salt -continued 4-[2-(3-Aminopyrazolo[1,5-a]pyridin-2-ylamino)ethyl]-1-methyl-1-propylpiperazin-1-ium salt 4-(3-Aminopyrazolo[1,5-a]pyridin-2-yl)-1-(2-hydroxyethyl)piperazin-1-ium salt

[4-(3-Aminopyrazolo[1,5-a]pyridin-2-ylamino)phenyl]trimethylammonium salt

3-[3-(3-Aminopyrazolo[1,5-a]pyridin-2-yloxy)propyl]-1-methyl-3H-imidazol-1-ium salt 4-(3-Aminopyrazolo[1,5-a]pyridin-2-yl)-1,1-dimethyl-[1,4]-diazepan-1-ium salt

[2-(3-Amino-6,7-dimethylpyrazolo[1,5-a]pyridine-2-ylamino)ethyl]trimethylammonium salt -continued

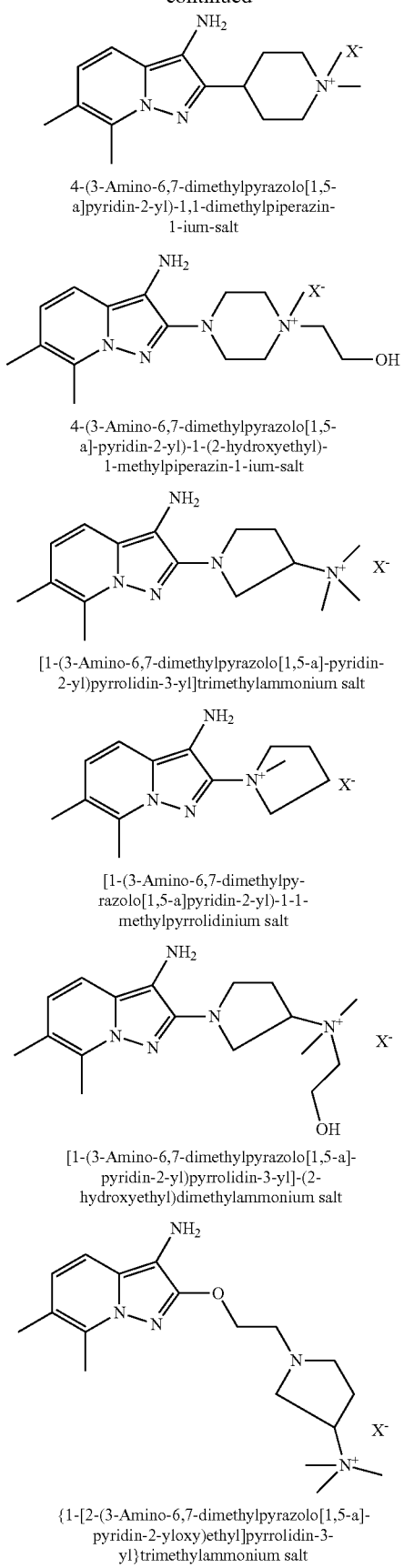

4-(3-Amino-6,7-dimethylpyrazolo[1,5-a]pyridin-2-yl)-1,1-dimethylpiperazin-1-ium-salt 4-(3-Amino-6,7-dimethylpyrazolo[1,5-a]-pyridin-2-yl)-1-(2-hydroxyethyl)-1-methylpiperazin-1-ium-salt

[1-(3-Amino-6,7-dimethylpyrazolo[1,5-a]-pyridin-2-yl)pyrrolidin-3-yl]trimethylammonium salt

[1-(3-Amino-6,7-dimethylpyrazolo[1,5-a]pyridin-2-yl)-1-1-methylpyrrolidinium salt

[1-(3-Amino-6,7-dimethylpyrazolo[1,5-a]-pyridin-2-yl)pyrrolidin-3-yl]-(2-hydroxyethyl)dimethylammonium salt {1-[2-(3-Amino-6,7-dimethylpyrazolo[1,5-a]-pyridin-2-yloxy)ethyl]pyrrolidin-3-yl}trimethylammonium salt -continued

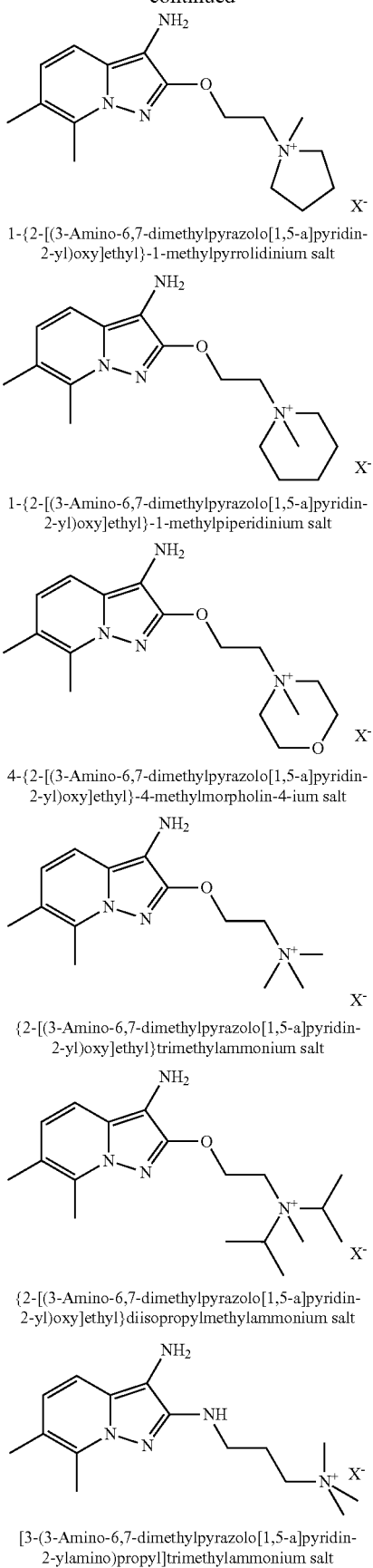

1-{2-[(3-Amino-6,7-dimethylpyrazolo[1,5-a]pyridin-2-yl)oxy]ethyl}-1-methylpyrrolidinium salt 1-{2-[(3-Amino-6,7-dimethylpyrazolo[1,5-a]pyridin-2-yl)oxy]ethyl}-1-methylpiperidinium salt 4-{2-[(3-Amino-6,7-dimethylpyrazolo[1,5-a]pyridin-2-yl)oxy]ethyl}-4-methylmorpholin-4-ium salt {2-[(3-Amino-6,7-dimethylpyrazolo[1,5-a]pyridin-2-yl)oxy]ethyl}trimethylammonium salt {2-[(3-Amino-6,7-dimethylpyrazolo[1,5-a]pyridin-2-yl)oxy]ethyl}diisopropylmethylammonium salt

[3-(3-Amino-6,7-dimethylpyrazolo[1,5-a]pyridin-2-ylamino)propyl]trimethylammonium salt -continued

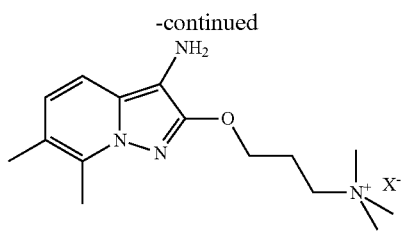

[3-(3-Amino-6,7-dimethylpyrazolo[1,5-a]pyridin-2-yloxy)propyl]trimethylammonium salt

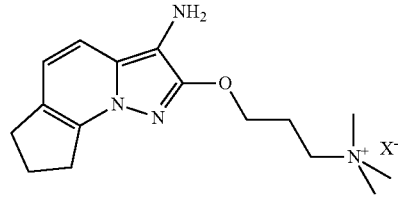

[3-(3-Amino-7,8-dihydro-6H-cyclopenta[e]pyrazolo[1,5-a]pyridin-2-yloxy)propyl]trimethyl-ammonium salt

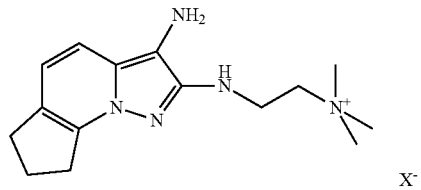

{2-[(3-Amino-7,8-dihydro-6H-cyclopenta[e]pyrazolo[1,5-a]pyridin-2-yl)amino]ethyl}trimethyl-ammonium salt

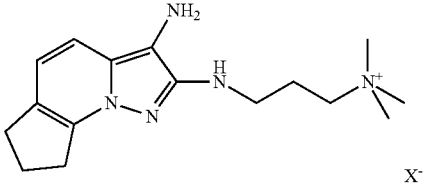

{3-[(3-Amino-7,8-dihydro-6H-cyclopenta[e]pyrazolo[1,5-a]pyridin-2-yl)amino]propyl}trimethyl-ammonium salt

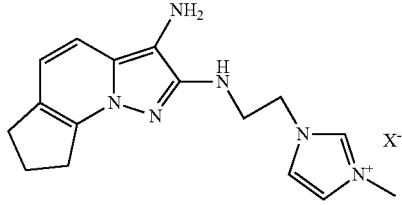

1-{2-[(3-Amino-7,8-dihydro-6H-cyclopenta[e]pyrazolo[1,5-a]pyridin-2-yl)amino]ethyl}-3-methyl-1H-imidazol-3-ium salt

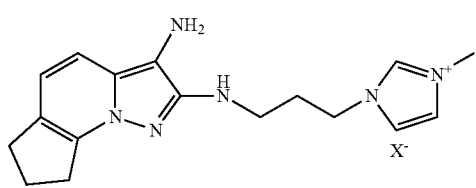

1-{3-[(3-Amino-7,8-dihydro-6H-cyclopenta[e]pyrazolo[1,5-a]pyridin-2-yl)amino]propyl}-3-methyl-1H-imidazol-3-ium salt -continued

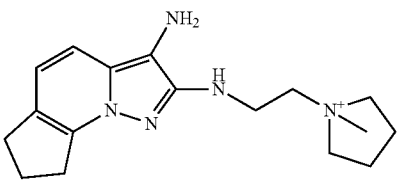

1-{2-[(3-Amino-7,8-dihydro-6H-cyclopenta[e]pyrazolo[1,5-a]pyridin-2-yl)amino]ethyl}-1-methylpyrrolidinium salt

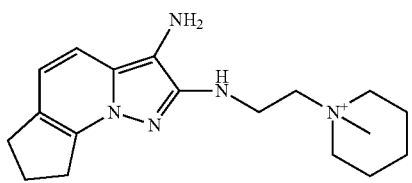

1-{2-[(3-Amino-7,8-dihydro-6H-cyclopenta[e]pyrazolo[1,5-a]pyridin-2-yl)amino]ethyl}-1-methylpiperidinium salt

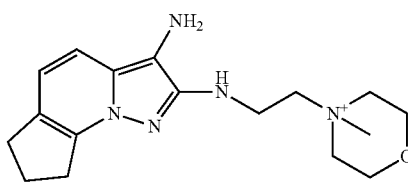

4-{2-[(3-Amino-7,8-dihydro-6H-cyclopenta[e]pyrazolo[1,5-a]pyridin-2-yl)amino]ethyl}-4-methylmorpholin-4-ium salt

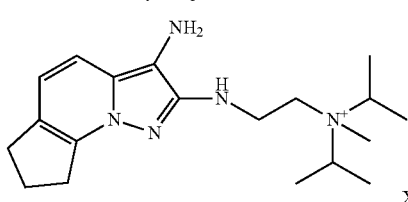

{2-[(3-Amino-7,8-dihydro-6H-cyclopenta[e]pyrazolo[1,5-a]pyridin-2-yl)amino]ethyl}diisopropyl-methylammonium salt

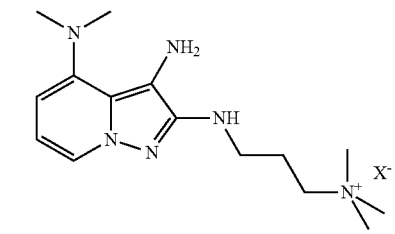

[3-(3-Amino-4-dimethylaminopyrazolo[1,5-a]pyridin-2-ylamino)propyl]trimethylammonium salt

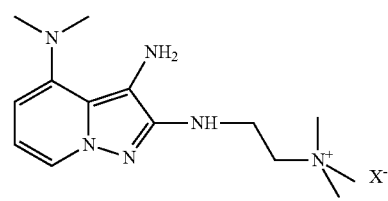

[2-(3-Amino-4-(dimethylamino)pyrazolo[1,5-a]pyridin-2-ylamino)ethyl]trimethylammonium salt -continued

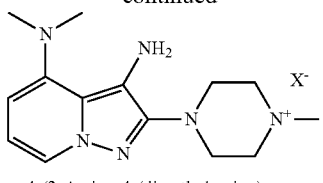

4-(3-Amino-4-(dimethylamino)pyrazolo[1,5-a]-pyridin-2-yl)-1-methylpiperazin-1-ium-salt

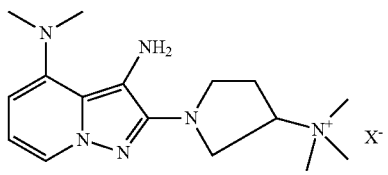

[1-(3-Amino-4-(dimethylamino)pyrazolo[1,5-a]-pyridin-2-yl)pyrrolidin-3-yl]trimethylammonium salt

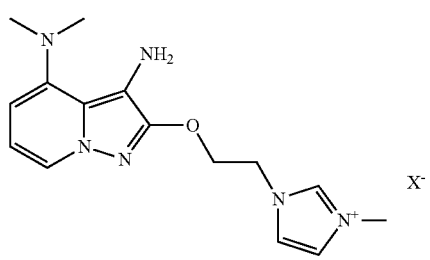

3-[2-(3-Amino-4-(dimethylamino)pyrazolo[1,5-a]-pyridin-2-yloxy)ethyl]-1-methyl-3H-imidazol-1-ium salt

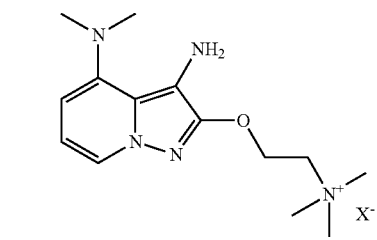

[2-(3-Amino-4-(dimethylamino)pyrazolo[1,5-a]-pyridin-2-yloxy)ethyl]trimethylammonium salt

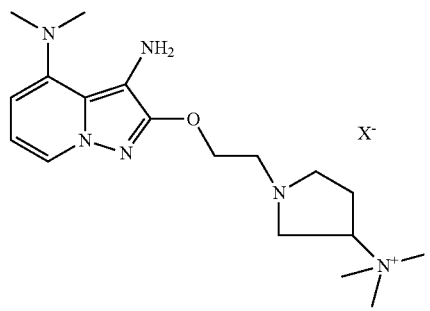

{1-[2-(3-Amino-4-dimethylamino)pyrazolo[1,5-a]-pyridin-2-yloxy)ethyl]pyrrolidin-3-yl}trimethylammonium salt -continued

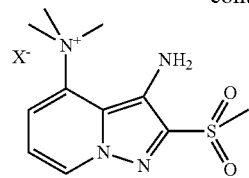

(3-Amino-2-(methanesulphonyl)pyrazolo[1,5-a]-pyridin-4-yl)trimethylammonium salt (3-Amino-2-(methoxy-pyrazolo[1,5-a]pyridin-4-yl)trimethylammonium salt and the addition salts, solvates, and solvates of the salts thereof.

15. The composition according to claim 1, wherein the compounds of formulae (I) and (II) are chosen from:

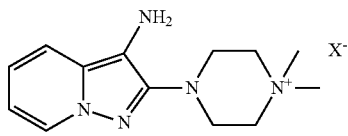

4-(3-aminopyrazolo[1,5-a]pyridin-2-yl)-1,1-dimethylpiperazin-1-ium salt

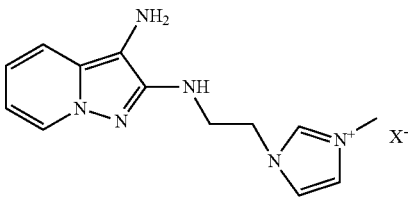

3-[2-(3-aminopyrazolo[1,5-a]pyridin-2-ylamino)ethyl]-1-methyl-3H-imidazol-1-ium salt and 2-[(3-aminopyrazolo[1,5-a]pyridin-2-yl)oxy]ethanol, and the addition salts, solvates, and solvates of the salts thereof.

16. The composition according to claim 1, wherein the at least one coupler is chosen from meta-phenylenediamines, meta-aminophenols, meta-diphenols, naphthalene couplers, heterocyclic couplers, and the addition salts, solvates, and solvates of the salts thereof.

17. A method for dyeing keratinous fibers, comprising applying to the keratinous fibers a composition comprising:
a) at least about 25% by weight of at least one fatty substance, wherein said at least one fatty substance does not comprise a carboxylic acid functional group;
b) at least one aminopyrazolopyridine oxidation base chosen from bases of formula (I), bases of formula (II), and the addition salts, solvates and solvates of the salts thereof:

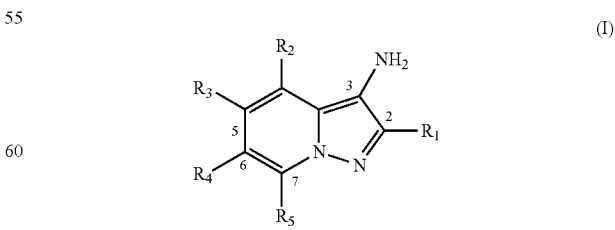

wherein:
$R_1$, $R_2$, $R_3$, $R_4$ and $R_5$, which are identical or different, are chosen from hydrogen atoms;

halogen atoms; —NHSO$_3$H radicals; hydroxyl radicals; (C$_1$-C$_4$)alkyl radicals; (C$_1$-C$_4$)alkoxy radicals; (C$_1$-C$_4$) alkylthio radicals; mono(C$_1$-C$_4$)alkylamino radicals; di(C$_1$-C$_4$)alkylamino radicals wherein the two alkyl groups can, in conjunction with the nitrogen atom to which they are bonded, form a ring which is optionally interrupted by at least one atom chosen from nitrogen, oxygen and sulphur atoms; heterocycles; nitro radicals; phenyl radicals; carbonyl radicals; alkoxy(C$_1$-C$_4$)carbonyl radicals; carboxamido radicals; cyano radicals; amino radicals; sulphonyl radicals; —CO$_2$H radicals; —SO$_3$H radicals; —PO$_3$H$_2$ radicals; —PO$_4$H$_2$ radical; and groups

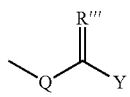

wherein R''' is chosen from oxygen and nitrogen atoms, Q is chosen from oxygen atoms, NH groups, and NH(C$_1$-C$_4$)alkyl groups, and Y is chosen from hydroxyl, amino, (C$_1$-C$_4$)alkyl, (C$_1$-C$_4$)alkoxy, (C$_1$-C$_4$)alkylamino and di(C$_1$-C$_4$)alkylamino radicals;

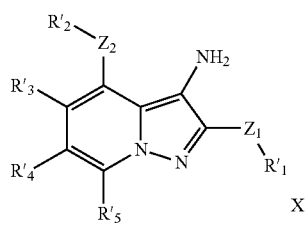

wherein:
Z$_1$ and Z$_2$, which may be identical or different, are chosen from single covalent bonds and divalent radicals chosen from:
—O(CH$_2$)$_p$— radicals, wherein p is an integer ranging from 0 to 6; and
—NR'$_6$(CH$_2$)$_q$(C$_6$H$_4$)$_t$— radicals, wherein q is an integer ranging from 0 to 6, t is chosen from 0 and 1, and R'$_6$ is chosen from hydrogen atoms and C$_1$-C$_6$ alkyl radicals optionally substituted by at least one hydroxyl group;
Z$_1$ may also be chosen from divalent radicals —S—, —SO— and —SO$_2$— when R'$_1$ is a methyl radical;
R'$_1$ and R'$_2$, which may be identical or different, are chosen from
hydrogen atoms;
C$_1$-C$_{10}$ alkyl radicals, optionally substituted and optionally interrupted by a group chosen from heteroatoms, O, N, Si, S, SO and SO$_2$;
halogen atoms;
SO$_3$H radicals;
substituted and unsubstituted and saturated, unsaturated and aromatic 5- to 8-membered rings optionally including at least one group chosen from heteroatoms, N, O, S, SO$_2$ and —CO—, wherein the ring may be at least one of cationic and substituted by a cationic radical;
—N$^+$R$_{17}$R$_{18}$R$_{19}$ groups, wherein R$_{17}$, R$_{18}$ and R$_{19}$ are chosen from linear and branched C$_1$-C$_5$ alkyls optionally substituted by at least one hydroxyl group;

when Z$_1$ or Z$_2$ respectively represents a covalent bond, then R'$_1$ or R'$_2$ can respectively be chosen from
optionally substituted C$_1$-C$_6$ alkylcarbonyl radicals;
—O—CO—R, —CO—O—R, NR—CO—R' and —CO—NRR' radicals wherein R and R', which may be identical or different, are chosen from hydrogen atoms and optionally substituted C$_1$-C$_6$ alkyl radicals;
R'$_3$, R'$_4$ and R'$_5$, which may be identical or different, are chosen from
hydrogen atoms;
hydroxyl radicals;
C$_1$-C$_6$ alkoxy radicals;
C$_1$-C$_6$ alkylthio radicals;
amino radicals;
monoalkylamino radicals;
di(C$_1$-C$_6$)alkylamino radicals wherein the alkyl radicals can form, with the nitrogen atom to which they are attached, an optionally saturated and optionally aromatic 5- to 8-membered heterocycle which can include at least one group chosen from heteroatoms, N, O, S, SO$_2$ and CO, it being possible for the heterocycle to be at least one of cationic and substituted by a cationic radical;
optionally substituted C$_1$-C$_6$ alkylcarbonyl radicals;
—O—CO—R, —CO—O—R, NR—CO—R' and —CO—NRR' radicals wherein R and R', which may be identical or different, are chosen from hydrogen atoms and optionally substituted C$_1$-C$_6$ alkyl radicals;
halogen atoms;
—NHSO$_3$H radicals;
optionally substituted C$_1$-C$_4$ alkyl radicals;
saturated, unsaturated and aromatic carbon rings which are optionally substituted;
R'$_3$, R'$_4$ and R'$_5$ can form, in pairs, a ring which is optionally partially saturated;
X is chosen from ions and groups of ions which makes it possible to provide the electrical neutrality of the derivative of formula (II);
wherein at least one of the groups R'$_1$ and R'$_2$ is a cationic radical;
c) at least one coupler; and
d) at least one oxidizing agent.
18. A two-compartment device comprising:
in a first compartment, a first composition comprising
a) at least 25% by weight of at least one fatty substance, wherein said at least one fatty substance does not comprise a carboxylic acid functional group,
b) at least one aminopyrazolopyridine oxidation base chosen from bases of formula (I), bases of formula (II), and the addition salts, solvates and solvates of the salts thereof:

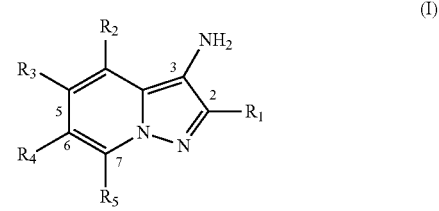

wherein:
R$_1$, R$_2$, R$_3$, R$_4$ and R$_5$, which are identical or different, are chosen from hydrogen atoms; halogen atoms; —NHSO$_3$H radicals; hydroxyl radicals; (C$_1$-C$_4$)alkyl radicals; ($C_1$-$C_4$)alkoxy radicals; ($C_1$-$C_4$)alkylthio radicals; mono($C_1$-$C_4$)alkylamino radicals; di($C_1$-$C_4$)alkylamino radicals wherein the two alkyl groups can, in conjunction with the nitrogen atom to which they are bonded, form a ring which is optionally interrupted by at least one atom chosen from nitrogen, oxygen and sulphur atoms; heterocycles; nitro radicals; phenyl radicals; carbonyl radicals; alkoxy($C_1$-$C_4$)carbonyl radicals; carboxamido radicals; cyano radicals; amino radicals; sulphonyl radicals; —$CO_2H$ radicals; —$SO_3H$ radicals; —$PO_3H_2$ radicals; —$PO_4H_2$ radical; and groups

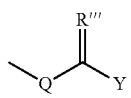

wherein R''' is chosen from oxygen and nitrogen atoms, Q is chosen from oxygen atoms, NH groups, and NH($C_1$-$C_4$)alkyl groups, and Y is chosen from hydroxyl, amino, ($C_1$-$C_4$)alkyl, ($C_1$-$C_4$)alkoxy, ($C_1$-$C_4$)alkylamino and di($C_1$-$C_4$)alkylamino radicals;

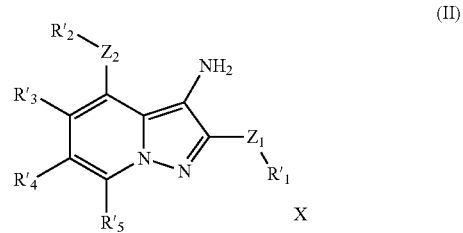

wherein:
$Z_1$ and $Z_2$, which may be identical or different, are chosen from single covalent bonds and divalent radicals chosen from:
—$O(CH_2)_p$— radicals, wherein p is an integer ranging from 0 to 6; and
—$NR'_6(CH_2)_q(C_6H_4)_t$— radicals, wherein q is an integer ranging from 0 to 6, t is chosen from 0 and 1, and $R'_6$ is chosen from hydrogen atoms and $C_1$-$C_6$ alkyl radicals optionally substituted by at least one hydroxyl group;
$Z_1$ may also be chosen from divalent radicals —S—, —SO— and —$SO_2$— when $R'_1$ is a methyl radical;
$R'_1$ and $R'_2$, which may be identical or different, are chosen from
hydrogen atoms;
$C_1$-$C_{10}$ alkyl radicals, optionally substituted and optionally interrupted by a group chosen from heteroatoms, O, N, Si, S, SO and $SO_2$;
halogen atoms;
$SO_3H$ radicals;
substituted and unsubstituted and saturated, unsaturated and aromatic 5- to 8-membered rings optionally including at least one group chosen from heteroatoms, N, O, S, $SO_2$ and —CO—, wherein the ring may be at least one of cationic and substituted by a cationic radical;
—$N^+R_{17}R_{18}R_{19}$ groups, wherein $R_{17}$, $R_{18}$ and $R_{19}$ are chosen from linear and branched $C_1$-$C_5$ alkyls optionally substituted by at least one hydroxyl group;
when $Z_1$ or $Z_2$ respectively represents a covalent bond, then $R'_1$ or $R'_2$ can respectively be chosen from
optionally substituted $C_1$-$C_6$ alkylcarbonyl radicals;
—O—CO—R, —CO—O—R, NR—CO-R' and —CO-NRR' radicals wherein R and R', which may be identical or different, are chosen from hydrogen atoms and optionally substituted $C_1$-$C_6$ alkyl radicals;
$R'_3$, $R'_4$ and $R'_5$, which may be identical or different, are chosen from
hydrogen atoms;
hydroxyl radicals;
$C_1$-$C_6$ alkoxy radicals;
$C_1$-$C_6$ alkylthio radicals;
amino radicals;
monoalkylamino radicals;
di($C_1$-$C_6$) alkylamino radicals wherein the alkyl radicals can form, with the nitrogen atom to which they are attached, an optionally saturated and optionally aromatic 5- to 8-membered heterocycle which can include at least one group chosen from heteroatoms, N, O, S, $SO_2$ and CO, it being possible for the heterocycle to be at least one of cationic and substituted by a cationic radical;
optionally substituted $C_1$-$C_6$ alkylcarbonyl radicals;
—O—CO—R, —CO—O—R, NR—CO—R' and —CO-NRR' radicals wherein R and R', which may be identical or different, are chosen from hydrogen atoms and optionally substituted $C_1$-$C_6$ alkyl radicals;
halogen atoms;
—$NHSO_3H$ radicals;
optionally substituted $C_1$-$C_4$ alkyl radicals;
saturated, unsaturated and aromatic carbon rings which are optionally substituted;
$R'_3$, $R'_4$ and $R'_5$ can form, in pairs, a ring which is optionally partially saturated;
X is chosen from ions and groups of ions which makes it possible to provide the electrical neutrality of the derivative of formula (II);
wherein at least one of the groups $R'_1$ and $R'_2$ is a cationic radical; and
c) at least one coupler; and,
in a second compartment, a second composition comprising at least one oxidizing agent.
19. A three-compartment device comprising:
in a first compartment, a first composition comprising at least 25% by weight of at least one fatty substance, wherein said at least one fatty substance does not comprise a carboxylic acid functional group;
in a second compartment, a second composition comprising:
a) at least one aminopyrazolopyridine oxidation base chosen from bases of formula (I), bases of formula (II), and the addition salts, solvates and solvates of the salts thereof:

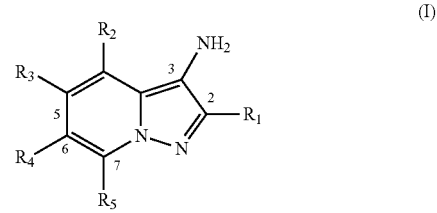

wherein:
$R_1$, $R_2$, $R_3$, $R_4$ and $R_5$, which are identical or different, are chosen from hydrogen atoms; halogen atoms; —$NHSO_3H$ radicals; hydroxyl radicals; ($C_1$-$C_4$)alkyl radicals; (C₁-C₄)alkoxy radicals; (C₁-C₄)alkylthio radicals; mono(C₁-C₄)alkylamino radicals; di(C₁-C₄)alkylamino radicals wherein the two alkyl groups can, in conjunction with the nitrogen atom to which they are bonded, form a ring which is optionally interrupted by at least one atom chosen from nitrogen, oxygen and sulphur atoms; heterocycles; nitro radicals; phenyl radicals; carbonyl radicals; alkoxy(C₁-C₄)carbonyl radicals; carboxamido radicals; cyano radicals; amino radicals; sulphonyl radicals; —CO₂H radicals; —SO₃H radicals; —PO₃H₂ radicals; —PO₄H₂ radical; and groups

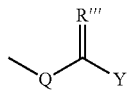

wherein R''' is chosen from oxygen and nitrogen atoms, Q is chosen from oxygen atoms, NH groups, and NH(C₁-C₄)alkyl groups, and Y is chosen from hydroxyl, amino, (C₁-C₄)alkyl, (C₁-C₄)alkoxy, (C₁-C₄)alkylamino and di(C₁-C₄)alkylamino radicals;

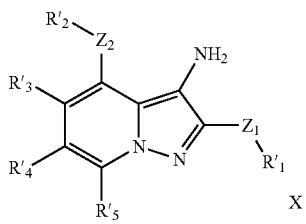
(II)

wherein:
Z₁ and Z₂, which may be identical or different, are chosen from single covalent bonds and divalent radicals chosen from:
—O(CH₂)$_p$— radicals, wherein p is an integer ranging from 0 to 6; and
—NR'₆(CH₂)$_q$(C₆H₄)$_t$— radicals, wherein q is an integer ranging from 0 to 6, t is chosen from 0 and 1, and R'₆ is chosen from hydrogen atoms and C₁-C₆ alkyl radicals optionally substituted by at least one hydroxyl group;
Z₁ may also be chosen from divalent radicals —S—, —SO— and –SO₂— when R'₁ is a methyl radical;
R'₁ and R'₂, which may be identical or different, are chosen from
hydrogen atoms;
C₁-C₁₀ alkyl radicals, optionally substituted and optionally interrupted by a group chosen from heteroatoms, O, N, Si, S, SO and SO₂;
halogen atoms;
SO₃H radicals;
substituted and unsubstituted and saturated, unsaturated and aromatic 5- to 8-membered rings optionally including at least one group chosen from heteroatoms, N, O, S, SO₂ and —CO—, wherein the ring may be at least one of cationic and substituted by a cationic radical;
—N⁺R₁₇R₁₈R₁₉ groups, wherein R₁₇, R₁₈ and R₁₉ are chosen from linear and branched C₁-C₅ alkyls optionally substituted by at least one hydroxyl group;
when Z₁ or Z₂ respectively represents a covalent bond, then R'₁ or R'₂ can respectively be chosen from
optionally substituted C₁-C₆ alkylcarbonyl radicals;
—O—CO—R, —CO—O—R, NR—CO—R' and —CO—NRR' radicals wherein R and R', which may be identical or different, are chosen from hydrogen atoms and optionally substituted C₁-C₆ alkyl radicals;
R'₃, R'₄ and R'₅, which may be identical or different, are chosen from
hydrogen atoms;
hydroxyl radicals;
C₁-C₆ alkoxy radicals;
C₁-C₆ alkylthio radicals;
amino radicals;
monoalkylamino radicals;
di(C₁-C₆) alkylamino radicals wherein the alkyl radicals can form, with the nitrogen atom to which they are attached, an optionally saturated and optionally aromatic 5- to 8-membered heterocycle which can include at least one group chosen from heteroatoms, N, O, S, SO₂ and CO, it being possible for the heterocycle to be at least one of cationic and substituted by a cationic radical;
optionally substituted C₁-C₆ alkylcarbonyl radicals;
—O—CO—R, —CO—O—R, NR—CO—R' and —CO—NRR' radicals wherein R and R', which may be identical or different, are chosen from hydrogen atoms and optionally substituted C₁-C₆ alkyl radicals;
halogen atoms;
—NHSO₃H radicals;
optionally substituted C₁-C₄ alkyl radicals;
saturated, unsaturated and aromatic carbon rings which are optionally substituted;
R'₃, R'₄ and R'₅ can form, in pairs, a ring which is optionally partially saturated;
X is chosen from ions and groups of ions which makes it possible to provide the electrical neutrality of the derivative of formula (II);
wherein at least one of the groups R'₁ and R'₂ is a cationic radical; and
b) at least one coupler; and
in a third compartment, a third composition comprising at least one oxidizing agent.

* * * * *